(12) United States Patent
Rodriguez et al.

(10) Patent No.: US 11,272,884 B2
(45) Date of Patent: Mar. 15, 2022

(54) LINER FOR ADHESIVE SKIN PATCH

(71) Applicant: MEDTRONIC MINIMED, INC., Northridge, CA (US)

(72) Inventors: Jasson Rodriguez, Rosemead, CA (US); Ellis Garai, Studio City, CA (US); Ravi R. Deverkadra, Simi Valley, CA (US); Sara M. Voisin, Chatsworth, CA (US); Jacob E. Pananen, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 16/892,866

(22) Filed: Jun. 4, 2020

(65) Prior Publication Data

US 2021/0378592 A1 Dec. 9, 2021

(51) Int. Cl.
*A61B 5/00* (2006.01)
*A61B 5/145* (2006.01)
*A61B 5/1486* (2006.01)

(52) U.S. Cl.
CPC .......... *A61B 5/6833* (2013.01); *A61B 5/1486* (2013.01); *A61B 5/14532* (2013.01); *A61B 5/14865* (2013.01); *A61B 5/68335* (2017.08); *A61B 2560/0443* (2013.01); *A61B 2560/063* (2013.01)

(58) Field of Classification Search
CPC .......... A61B 2562/242; A61B 2562/24; A61B 2562/247; A61B 2562/16; A61B 2562/164; A61B 2560/063; A61B 2560/0412; A61B 2560/0443; A61B 2560/0431; A61B 5/145; A61B 5/150969; A61B 5/150206; A61B 5/150305; A61B 5/150267; A61B 5/15029; A61B 5/150297; A61B 5/150725; A61B 5/150717; A61B 5/14503; A61B 5/1451; A61B 5/14532; A61B 5/14546; A61B 5/1486–14865; A61B 5/6833–68335; A61F 13/00076; A61F 13/00085; A61F 13/00051; A61F 2013/00289; A61F 13/0259
See application file for complete search history.

(56) References Cited

U.S. PATENT DOCUMENTS

| 2,551,540 | A | * | 5/1951 | Erica | A01K 1/04 |
| | | | | | 119/786 |
| 4,755,173 | A | | 7/1988 | Konopka et al. | |
| 5,391,250 | A | | 2/1995 | Cheney, II et al. | |
| 5,485,408 | A | | 1/1996 | Blomquist | |

(Continued)

FOREIGN PATENT DOCUMENTS

| EP | 3199121 A1 * | 8/2017 | ............. B65B 55/04 |
| WO | WO-2012119131 A1 * | 9/2012 | ............. A61F 13/00 |
| WO | WO-2018222015 A1 * | 12/2018 | ............... A61B 5/15 |

*Primary Examiner* — Eric F Winakur
*Assistant Examiner* — Alice Ling Zou
(74) *Attorney, Agent, or Firm* — Lorenz & Kopf, LLP

(57) ABSTRACT

A liner associated with an adhesive skin patch of a physiological characteristic sensor deployed with a sensor inserter having a housing with a removable cover includes a surface to couple to the adhesive skin patch. The liner includes a removal portion to couple the liner to the removable cover of the sensor inserter such that a separation of the removable cover from the housing removes the liner from the adhesive skin patch.

14 Claims, 15 Drawing Sheets

(56) References Cited

U.S. PATENT DOCUMENTS

| | | |
|---|---|---|
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | McIvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,295,786 B2 | 3/2016 | Gottlieb et al. |
| 10,413,183 B2 | 9/2019 | Antonio et al. |
| 2007/0123819 A1 | 5/2007 | Mernoe et al. |
| 2009/0299301 A1 | 12/2009 | Gottlieb et al. |
| 2010/0160861 A1 | 6/2010 | Causey, III et al. |
| 2013/0150691 A1* | 6/2013 | Pace ............... A61B 5/150022 600/347 |
| 2017/0112534 A1* | 4/2017 | Schoonmaker ...... A61B 5/0004 |
| 2017/0251958 A1* | 9/2017 | Pushpala ................ A61B 5/685 |
| 2017/0290533 A1 | 10/2017 | Antonio et al. |
| 2019/0060511 A1* | 2/2019 | Larson ................. A61B 5/6833 |
| 2021/0137424 A1* | 5/2021 | Chae ...................... A61B 5/155 |

* cited by examiner

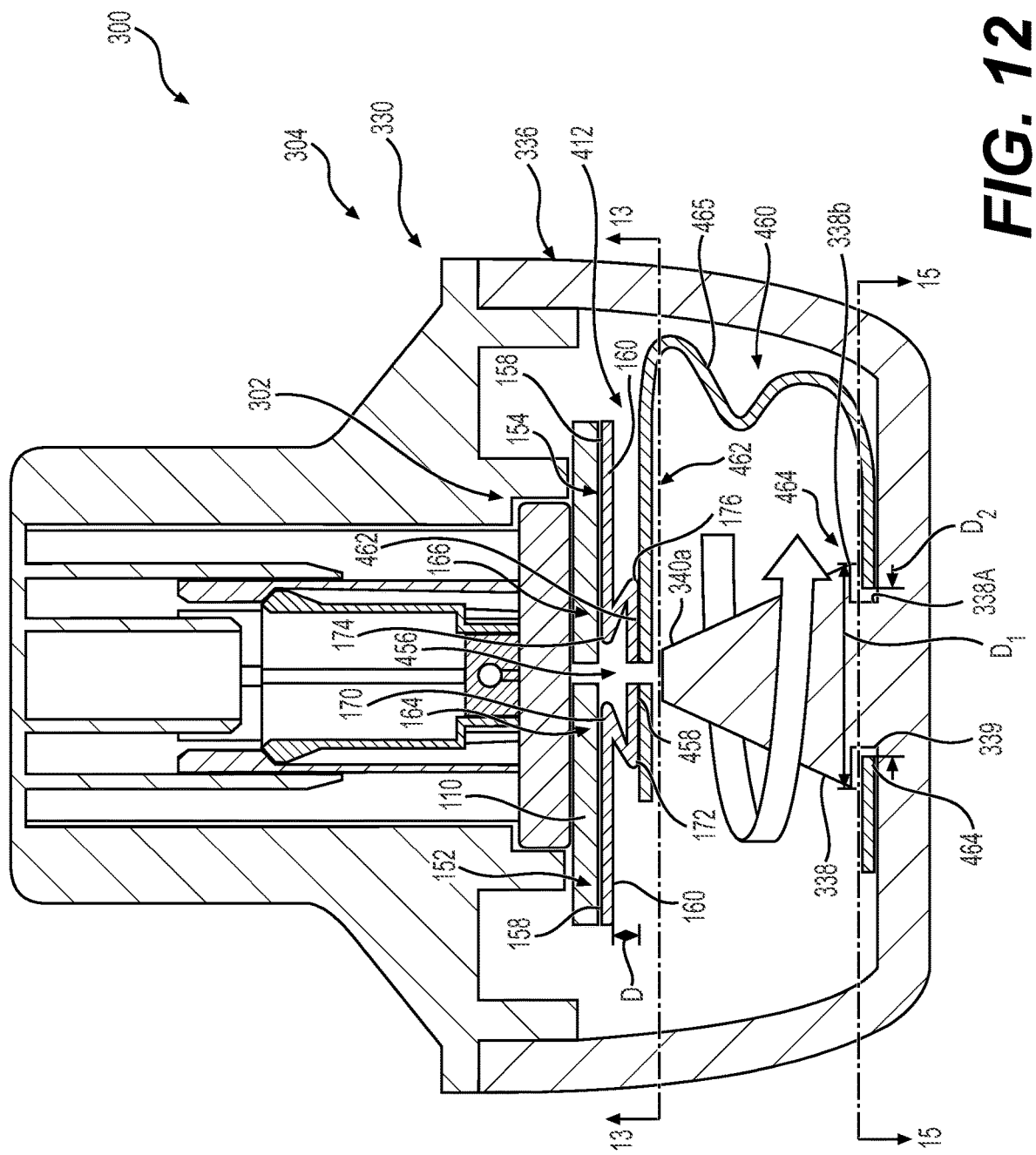

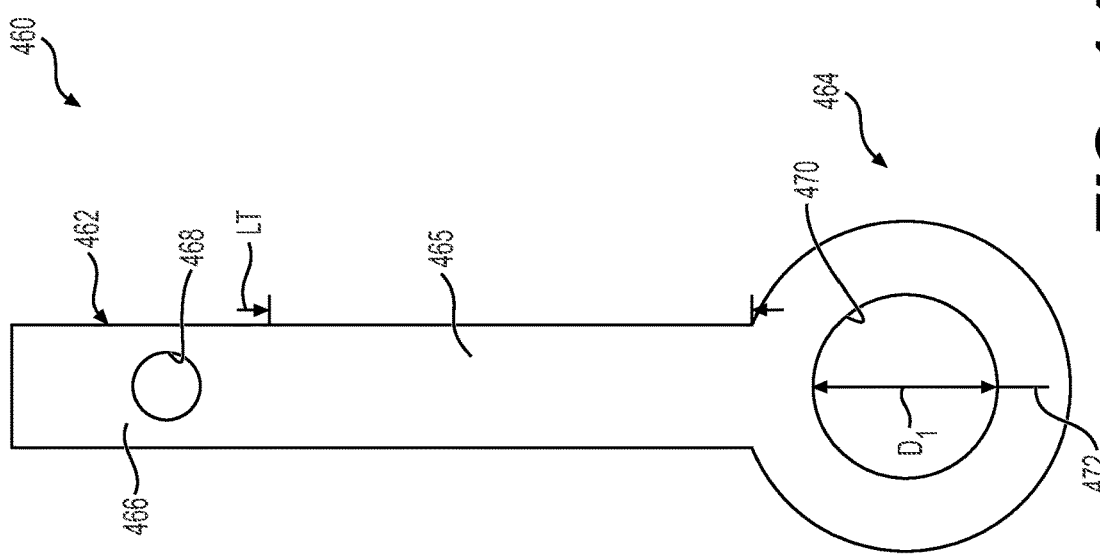
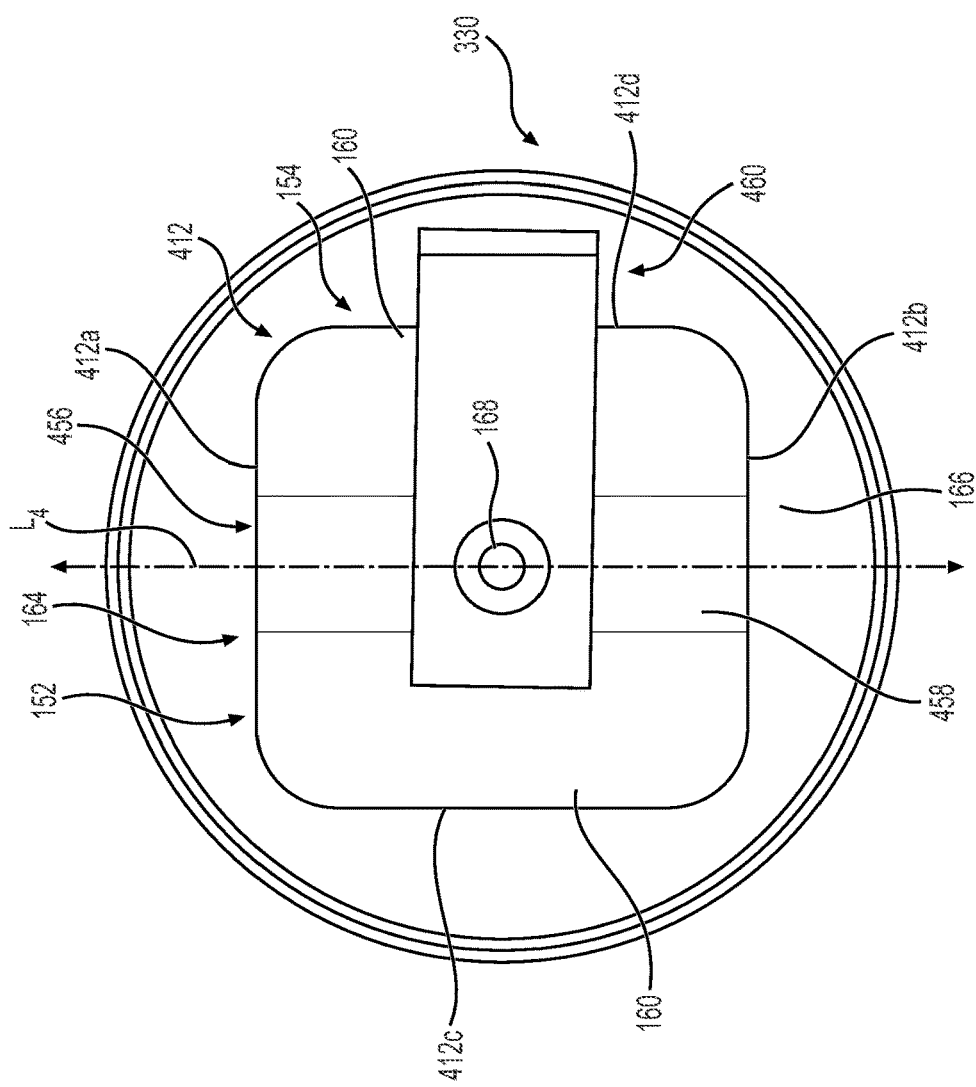

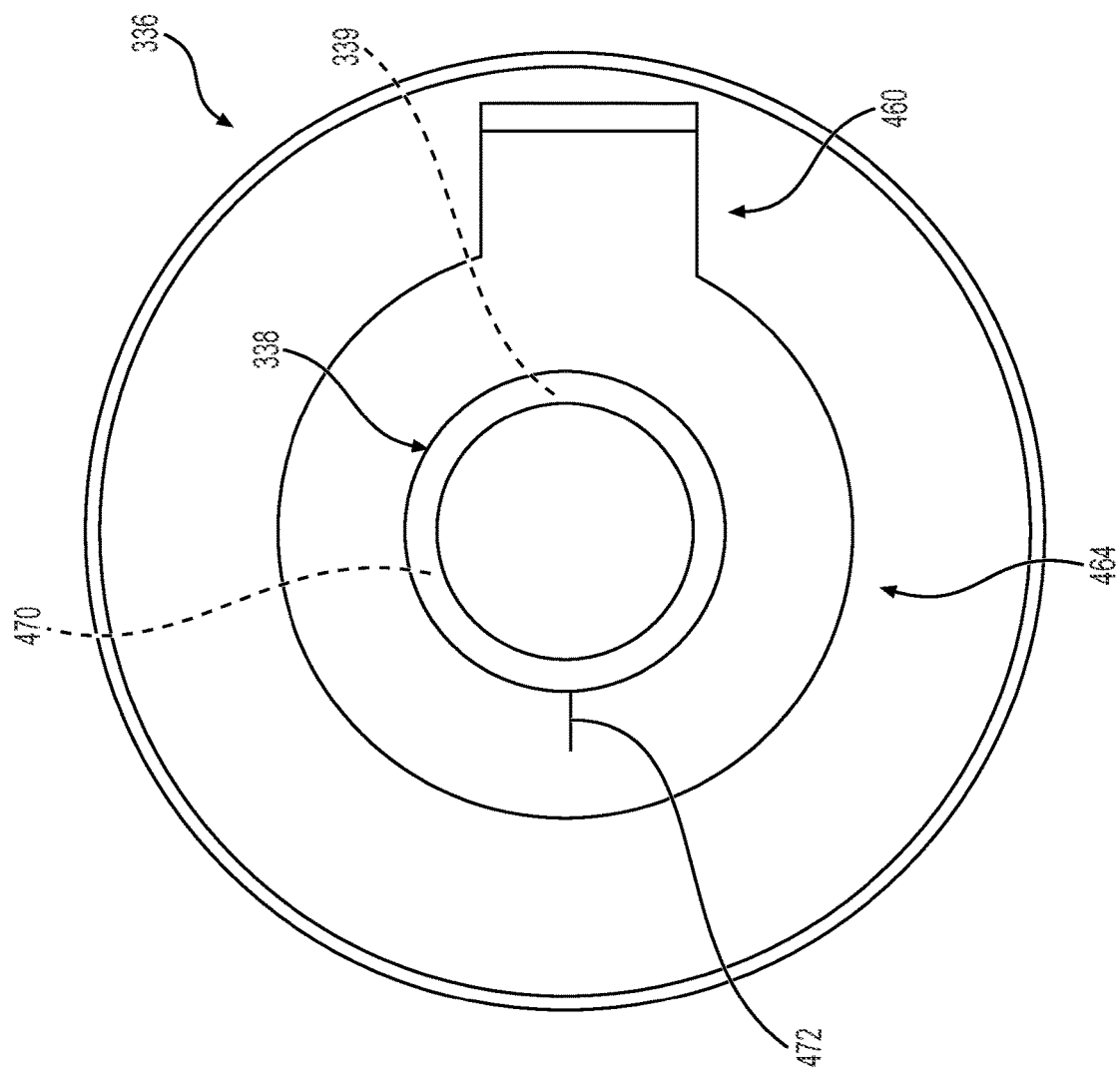

LINER FOR ADHESIVE SKIN PATCH

FIELD

Embodiments of the subject matter described herein relate generally to medical devices, such as a liner of an adhesive skin patch for a physiological characteristic sensor assembly. More particularly, embodiments of the subject matter relate to a liner that is removable from an adhesive skin patch with ease.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

A glucose sensor of the type described above may be packaged and sold as a product, such as a continuous glucose monitor, which is adhered to the patient during use via an adhesive skin patch. In certain instances, the continuous glucose monitor may be packaged with a sensor introducer tool, which enables the implantation of the glucose sensor subcutaneously/transcutaneously. The sensor introducer tool contains a needle that is used to puncture the skin of a user at the same time as the sensor is introduced. The needle is then withdrawn, leaving the sensor in the skin of the user.

In instances where the continuous glucose monitor is packaged with the sensor introducer tool, the continuous glucose monitor may be positioned within the sensor introducer tool such that the adhesive skin patch is covered with a liner to protect the adhesive skin patch during shipping. Once received by the user, the liner must be removed to adhere the continuous glucose monitor to the body of the user. In certain instances, the removal of the liner may be burdensome to the user. Further, in certain instances, the user may inadvertently contact the adhesive skin patch during the removal of the liner, which may impact the performance of the adhesive skin patch. In addition, the liner may be positioned about the needle of the sensor introducer tool, and the removal of the liner may result in the user inadvertently contacting the needle.

Accordingly, it is desirable to provide a liner of an adhesive skin patch, such as an adhesive skin patch coupled to a physiological characteristic sensor, for example, a glucose sensor or continuous glucose monitor, which enables the user to remove the liner with ease and without contacting the adhesive skin patch or the needle of an associated sensor introducer tool. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to a removable liner for an adhesive skin patch, such as an adhesive skin patch coupled to a medical device, such as a glucose sensor or continuous glucose monitor.

According to various embodiments, provided is a liner associated with an adhesive skin patch of a physiological characteristic sensor. The liner includes a first end opposite a second end, and a first side opposite a second side. The liner includes a surface to couple to the adhesive skin patch, at least a portion of which extends from the first end to the second end. The liner includes at least one graspable member defined between the first side and the second side that extends beyond the first end or the second end to initiate a peel of the liner from the adhesive patch at a center of the liner.

Further provided is a liner associated with an adhesive skin patch of a physiological characteristic sensor. The liner includes a first end opposite a second end, and a first portion spaced apart from a second portion. The first portion and the second portion extend from the first end to the second end and each of the first portion and the second portion define a surface to couple to the adhesive skin patch. The liner includes a removal portion defined between the first portion and the second portion. The removal portion is spaced apart and uncoupled from the adhesive skin patch. The removal portion includes at least one graspable member that extends beyond the first end or the second end that is manipulatable to remove the liner from the adhesive skin patch.

Also provided is a liner associated with an adhesive skin patch of a physiological characteristic sensor. The liner includes a first end opposite a second end and a first portion spaced apart from a second portion. The first portion and the second portion extend from the first end to the second end and each of the first portion and the second portion define a surface to couple to the adhesive skin patch. The liner includes a slot defined through the liner from the first end to the second end. The slot is defined between the first portion and the second portion. The liner includes at least one graspable member that extends beyond the first end or the second end. The at least one graspable member is defined adjacent to the slot and manipulatable to remove the liner from the adhesive skin patch.

Further provided according to various embodiments is a liner associated with an adhesive skin patch of a physiological characteristic sensor deployed with a sensor inserter having a housing with a removable cover. The liner includes a surface to couple to the adhesive skin patch and a removal portion to couple the liner to the removable cover of the sensor inserter such that a separation of the removable cover from the housing removes the liner from the adhesive skin patch.

Also provided is a sensor introduction assembly. The sensor introduction assembly includes a physiological characteristic sensor having an adhesive skin patch and a sensor inserter having a housing for deploying the physiological characteristic sensor. The sensor inserter has a housing with a removable cover. The sensor introduction assembly includes a liner coupled to the adhesive skin patch and to the removable cover. The liner includes a tether that extends between the liner and the removable cover such that a separation of the removable cover from the housing removes the liner from the adhesive skin patch.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 12 is a perspective view of another exemplary sensor introduction system that includes a sensor inserter and a physiological characteristic sensor assembly having an adhesive skin patch and an exemplary liner according to various teachings of the present disclosure;

FIG. 13 is a cross-sectional view of the sensor introduction system of FIG. 12, taken along line 13-13 of FIG. 12, which illustrates the liner coupled to the adhesive skin patch and a first tether end of a tether associated with the liner coupled to the liner;

FIG. 14 is a front view of the tether associated with the liner of FIG. 12;

FIG. 15 is a cross-sectional view of the sensor introduction system of FIG. 12, taken along line 15-15 of FIG. 12, which illustrates a second tether end of the tether associated with the liner coupled to a cover of the sensor inserter;

DETAILED DESCRIPTION

Figure 2:
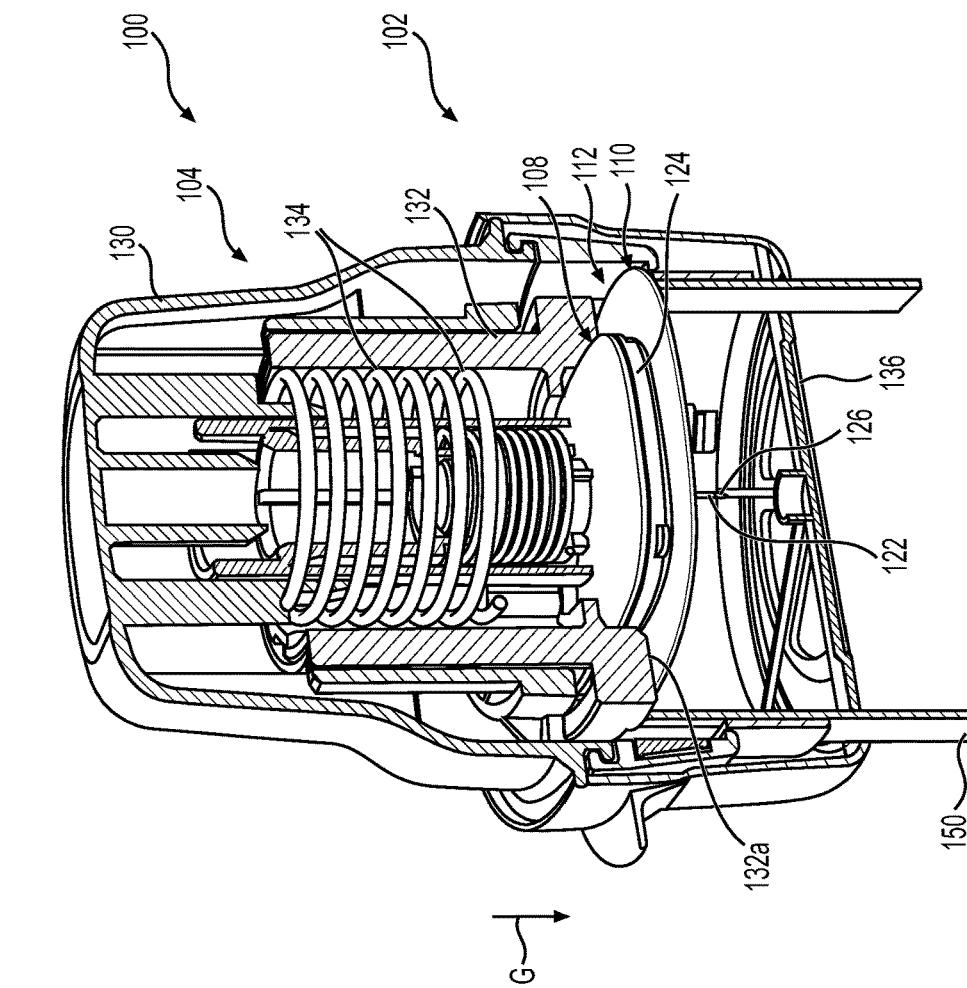
FIG. 2 is a cross-sectional view of the sensor introduction system of FIG. 1, taken along line 2-2 of FIG. 1.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

The following description relates to various embodiments of a removable liner for an adhesive skin patch. The liner of the adhesive skin patch described herein is removable with ease and substantially inhibits inadvertent contact with the adhesive skin patch or a needle of an associated sensor introducer tool. It should be noted that while the adhesive skin patch is described herein as being used with a glucose sensor, such as a glucose sensor associated with a continuous glucose monitor, it will be understood that the adhesive skin patch may be employed with a variety of other sensors, such as cardiac monitors, body temperature sensors, EKG monitors etc., medical devices, and/or other components that are intended to be affixed to the body of a user. Thus, while the non-limiting examples described below relate to a medical device used to treat diabetes (more specifically, an adhesive skin patch coupled to a continuous glucose monitor), embodiments of the disclosed subject matter are not so limited.

Generally, the glucose sensor employed with the adhesive skin patch is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein).

Figure 1:
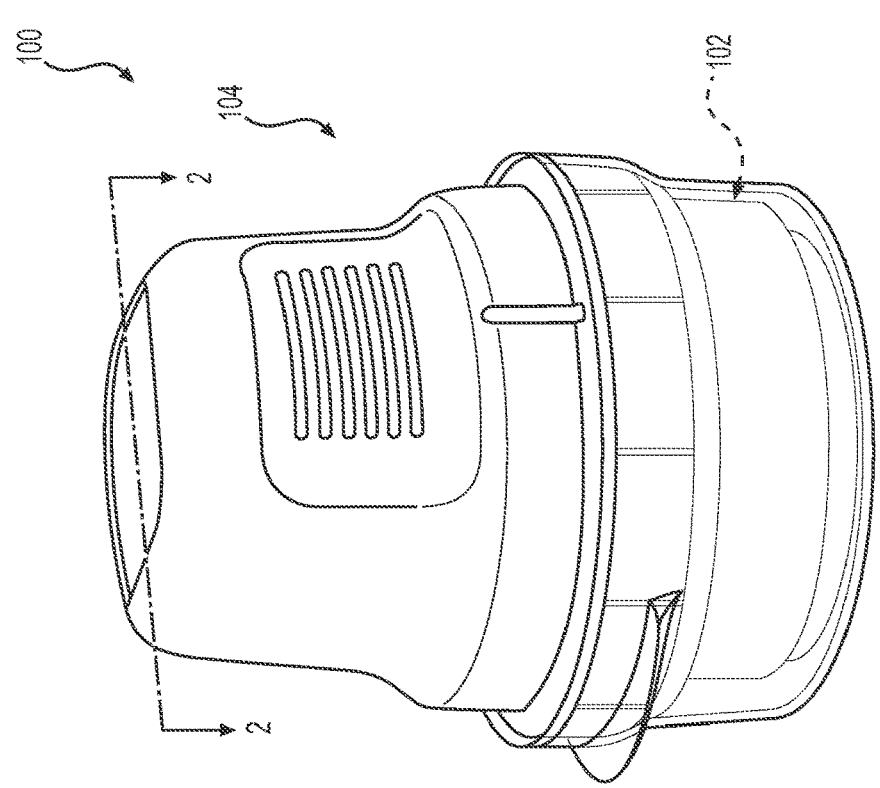
FIG. 1 is a perspective view of an exemplary sensor introduction system that includes a sensor inserter and a physiological characteristic sensor assembly having an adhesive skin patch and an exemplary liner according to various teachings of the present disclosure.

With reference to FIG. 1, FIG. 1 is a perspective view of a sensor introduction assembly 100. In one example, the sensor introduction assembly 100 includes a physiological characteristic sensor assembly 102 and a sensor inserter 104. In this example, with additional reference to FIG. 2, the physiological characteristic sensor assembly 102 includes a physiological characteristic sensor 108, an adhesive skin patch or adhesive patch 110 and a liner 112. Generally, the components of the physiological characteristic sensor assembly 102 are coupled together as a single unit. The physiological characteristic sensor assembly 102 and the sensor inserter 104 may be packaged together for use by a consumer. It should be noted that in certain embodiments, the sensor inserter 104 and the physiological characteristic sensor 108 may comprise the insertion device and the sensor transmitter assembly described in commonly assigned U.S. Patent Publication No. 2017/0290533 to Antonio, et al., the relevant portion of which is incorporated herein by reference. In addition, certain features, aspects, and characteristics of the adhesive patch 110 may be conventional and, as such, will not be described in detail here.

Briefly, the physiological characteristic sensor 108 can be pre-connected as part of a sensor set, which could also include a sensor electronics module (not shown), such as a wireless transmitter that communicates with an infusion pump, a monitor device, or the like, which connects to the physiological characteristic sensor 108 after the insertion or deployment of a portion of the physiological characteristic sensor 108 in the body of the user. In one example, the physiological characteristic sensor 108 includes a glucose sensor 122 and a sensor base 124. It should be noted that the physiological characteristic sensor 108 is not limited to a glucose sensor, but rather, various other physiological characteristic sensors may be employed. The glucose sensor 122 may be provided as an integral part of the sensor base 124. The sensor base 124 gives structural support to the glucose sensor 122, and facilitates entry of the glucose sensor 122 into the body of the user. The glucose sensor 122 is an electrochemical sensor that includes the glucose oxidase enzyme, as is well understood by those familiar with glucose sensor technology. The glucose oxidase enzyme enables the glucose sensor 122 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. Generally, the glucose sensor 122 is positionable in subcutaneous tissue of the user by an insertion needle 126 of the sensor inserter 104 to measure the glucose oxidase enzyme.

The sensor base 124 is coupled to the sensor inserter 104 and is coupled to the adhesive patch 110. The sensor base 124 is removably coupled to the sensor inserter 104. The sensor base 124 may also feature electrical and physical interfaces and elements that accommodate the sensor electronics module, such as the wireless transmitter that communicates with the infusion pump, the monitor device, or the like. In certain embodiments the sensor base 124 is composed at least in part from a plastic material. For the embodiment described here, the bulk of the sensor base 124 is formed as a molded plastic component. In one example, the sensor base 124 is formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like.

The adhesive patch 110 is coupled to the sensor base 124 and affixes the sensor base 124, and thus, the glucose sensor 122, to an anatomy, such as the skin of the user. The adhesive patch 110 is contained within the sensor inserter 104 during packaging and shipping, and is covered and protected by the liner 112. The adhesive patch 110 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

The sensor inserter 104 is coupled to the physiological characteristic sensor 108 and is manipulatable by a user to couple the glucose sensor 122 to the user. With continued reference to FIG. 2, the sensor inserter 104 includes a housing 130, a cradle or monitor support 132, one or more biasing members or springs 134 and a lid or cover 136. In one example, the housing 130 surrounds the physiological characteristic sensor assembly 102 and encloses the physiological characteristic sensor assembly 102 to enable sterilization of the physiological characteristic sensor assembly 102, for example. The housing 130 may include one or more features, such as movable tabs, that cooperate with the monitor support 132 to deploy the physiological characteristic sensor 108 into the anatomy. The monitor support 132 is coupled to the physiological characteristic sensor 108, and is movable relative to the housing 130 to deploy the physiological characteristic sensor 108 into the anatomy. For example, the application of a force to the housing 130 may bias the tabs to release the monitor support 132 to enable a spring 134 associated with the monitor support 132 to drive the monitor support 132 to deploy the physiological characteristic sensor 108 into the anatomy. Once released, another spring 134b cooperates with the monitor support 132 to move a needle retractor 131 relative to the housing 130. The cover 136 surrounds a circumferentially open end of the housing 130, and encloses the housing 130.

Figure 4:
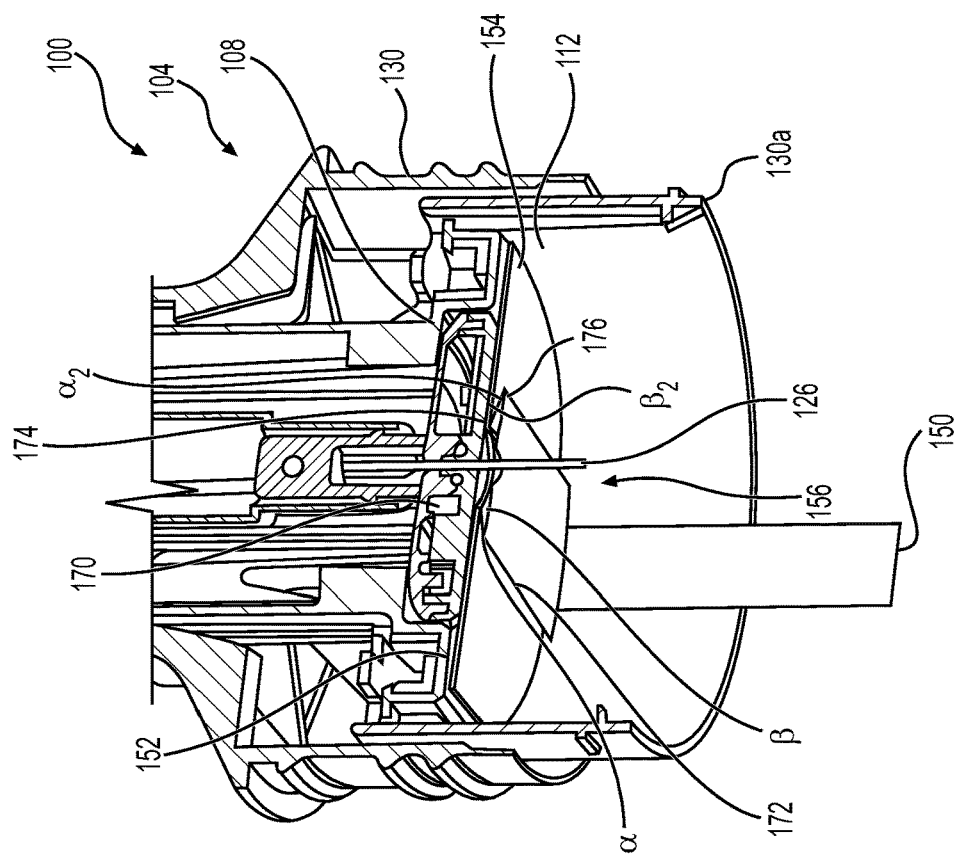
FIG. 4 is a cross-sectional view of the sensor introduction system of FIG. 1, taken along line 4-4 of FIG. 3.
Figure 3:
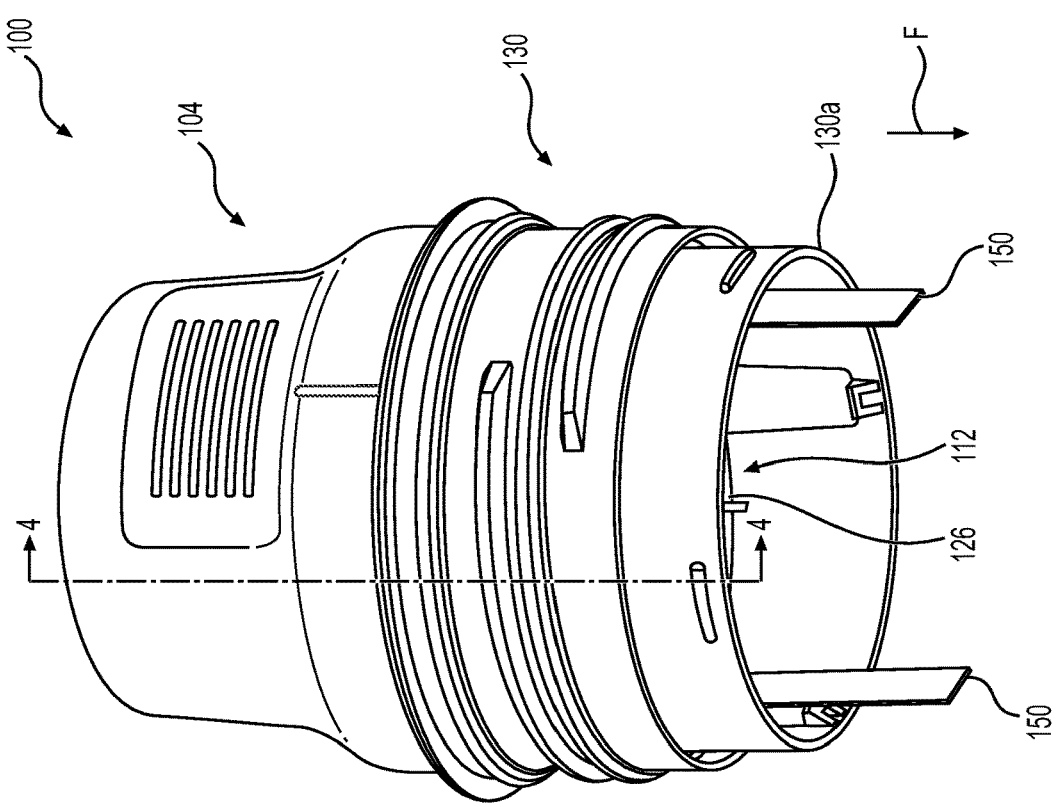
FIG. 3 is a perspective view of the sensor introduction system of FIG. 1, in which a cover has been removed to expose a portion of the liner.
Figure 5:
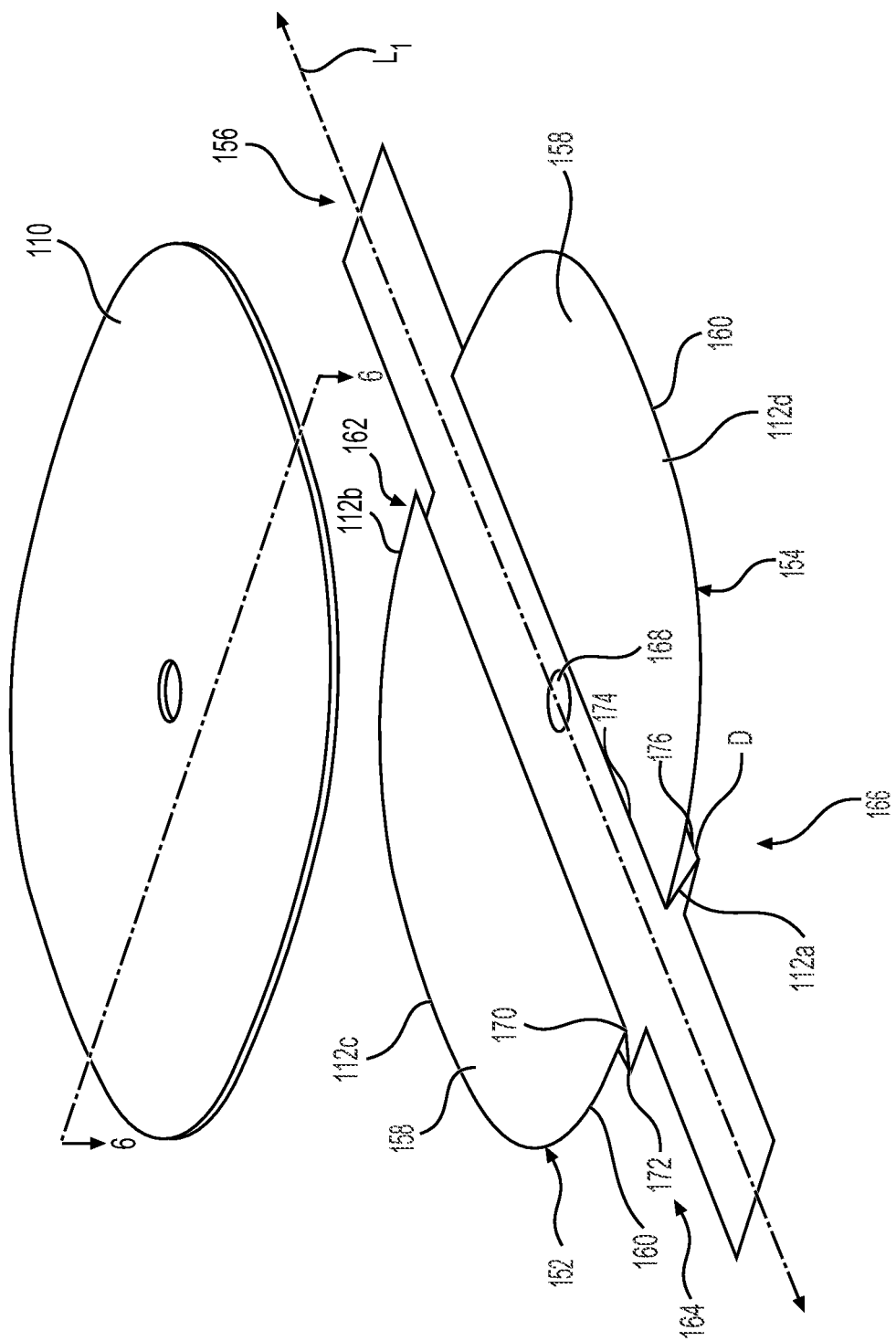
FIG. 5 is an exploded view of the adhesive skin patch and the liner associated with the sensor introduction system of FIG. 1.

In one example, with reference to FIG. 3, the liner 112 is shown in greater detail. FIG. 3 is a perspective view of the sensor inserter 104, which illustrates at least one graspable member or pull tabs 150 of the liner 112, which extend beyond a distalmost end 130a of the housing 130 when the cover 136 is removed. In this example, with reference to FIG. 4, the liner 112 is composed of a silicone coated paper or polymer film, and is coupled to the adhesive patch 110 so as to cover the adhesive patch 110 (FIG. 2). The liner 112 includes a first portion 152, a second portion 154 and a removal portion 156. With reference to FIG. 5, the first portion 152 is defined along a first side 112c of the liner 112, and the second portion 154 is defined along a second side 112d of the liner 112, the first side 112c opposite the second side 112d. Each of the sides 112c, 112d extend along a respective axis that is parallel to a longitudinal axis L1 of the liner 112, while each of ends 112a, 112b of the liner 112 extend along a respective axis that is perpendicular to the longitudinal axis L1. Each of the first portion 152 and the second portion 154 define a first surface 158 opposite a second surface 160. The first surface 158 is coupled to and contacts the adhesive patch 110. The second surface 160 faces the distalmost end 130a of the housing 130 (FIG. 4) and is exposed when the cover 136 (FIG. 2) is removed.

In this example, with reference to FIG. 5, the removal portion 156 is defined to extend along the longitudinal axis L1 of the liner 112. The removal portion 156 is defined between and coupled to each of the first portion 152 and the second portion 154. In one example, the removal portion 156 include the pull tabs 150 and a body section 162. In this example, the removal portion 156 includes two pull tabs 150, which extend from opposed ends of the body section 162. Stated another way, the pull tabs 150 extend beyond the first end 112a and the opposite second end 112b of the liner 112. The pull tabs 150 are sized to extend beyond the distalmost end 130a of the housing 130 (FIG. 2) when the liner 112 is coupled to the adhesive patch 110. By extending beyond the distalmost end 130a, each of the pull tabs 150 may be grasped by the user to remove the liner 112 from the adhesive patch 110 easily and without inadvertently contacting the adhesive patch 110 or the insertion needle 126 of the sensor inserter 104. The pull tabs 150 are defined on the liner 112 so as to be centered on the liner 112 between the first end 112a and the second end 112b. Stated another way, the pull tabs 150 are defined at a center of the liner 112.

Figure 6:
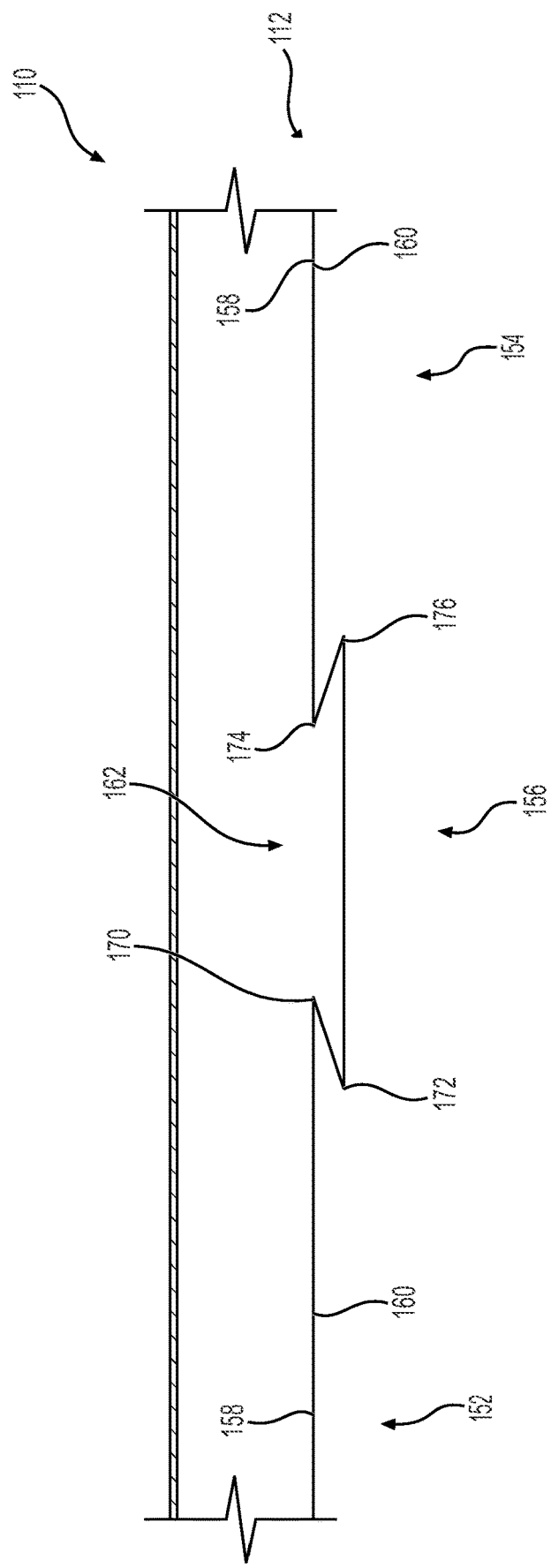
FIG. 6 is a cross-sectional view of the adhesive skin patch and the liner, taken along line 6-6 of FIG. 5.

The body section 162 is defined between the first portion 152 and the second portion 154 and extends from the first end 112a to the second end 112b of the liner 112. The body section 162 includes a first coupling portion 164, a second coupling portion 166 and defines a central bore 168. The central bore 168 is sized to enable the liner 112 to be positioned about the insertion needle 126. The first coupling portion 164 is defined between the body section 162 and the first portion 152 to couple the body section 162 to the first portion 152. The first coupling portion 164 is defined by a first fold 170 and a second fold 172 defined in the liner 112. In this example, with reference to FIG. 6, the first fold 170 and the second fold 172 define a Z-shape. Generally, the first fold 170 is defined by a negative angle, while the second fold 172 is defined by a positive angle. The first fold 170 and the second fold 172 reduce the force needed to peel the liner 112 from the adhesive patch 110, which enables the user to remove the liner 112 with ease.

With reference to FIG. 5, the second coupling portion 166 is defined to couple the body section 162 to the second portion 154. The second coupling portion 166 is defined by a third fold 174 and a fourth fold 176 defined in the liner 112. In this example, the third fold 174 and the fourth fold 176 define a Z-shape. In one example, the liner 112 is symmetric about the longitudinal axis L1. Generally, the third fold 174 is defined by a negative angle, while the fourth fold 176 is defined by a positive angle. The first fold 170, the second fold 172, the third fold 174 and the fourth fold 176 cooperate to distance the body section 162 from the adhesive patch 110 such that the body section 162 is not coupled to (uncoupled) and is spaced apart from the adhesive patch 110. In one example, the body section 162 is spaced a distance D of about two times the thickness of the liner 112 away from the first surface 158. Thus, the first fold 170 is spaced apart from the second fold 172 by the distance D, and the third fold 174 is spaced apart from the fourth fold 176 by the distance D.

By providing the body section 162 uncoupled from the adhesive patch 110, a removal force associated with separating the liner 112 from the adhesive patch 110 is reduced. In addition, the use of the first coupling portion 164 and the second coupling portion 166 ensures that the liner 112 is removed from the adhesive patch 110 starting from at the first fold 170 and the third fold 174 toward the sides 112c, 112d of the liner 112, which ensures that the liner 112 is removed from the adhesive patch 110 without inadvertently folding or rolling the adhesive patch 110. Stated another way, the peel of the liner 112 from the adhesive patch 110 starts along the longitudinal axis L1 at a center of the liner 112 between the first portion 152 and the second portion 154 or along the body section 162 at the ends 112a, 112b of the liner 112, and propagates outward to the sides 112c, 112d of the liner 112. By starting at the center of the liner 112 and propagating outward, the removal of the liner 112 reduces the likelihood of the adhesive patch 110 folding upon itself. In other words, if the liner 112 were removed from the sides 112c, 112d inward, the removal of the liner 112 may cause the adhesive patch 110 to fold, which may be undesirable for adhering to the body of the user. Thus, the removal portion 156 of the liner 112, by peeling from the center of the adhesive patch 110 toward the sides 112c, 112d, ensures that the adhesive patch 110 remains suitable for coupling to the user.

In one example, with the physiological characteristic sensor 108 assembled and coupled to the adhesive patch 110 and the liner 112 formed with the first fold 170, the second fold 172, the third fold 174 and the fourth fold 176, the first surface 158 of the first portion 152 and the second portion 154 of the liner 112 is coupled to the adhesive patch 110 such that the insertion needle 126 passes through the central bore 168. With the physiological characteristic sensor assembly 102 assembled, and the springs 134 and the monitor support 132 coupled to the housing 130, with reference to FIG. 3, the physiological characteristic sensor assembly 102 is coupled to the sensor inserter 104. The coupling of the physiological characteristic sensor assembly 102 to the sensor inserter 104 causes the pull tabs 150 to fold inward to be received within the housing 130 (FIG. 2). With the physiological characteristic sensor assembly 102 coupled to the sensor inserter 104, the cover 136 is coupled to the housing 130 to enclose the physiological characteristic sensor assembly 102 and the pull tabs 150 of the liner 112. The sensor inserter 104, including the physiological characteristic sensor assembly 102, may be sterilized and shipped to an end user.

Once received, the user may remove the cover 136 to expose the pull tabs 150. With reference to FIG. 3, the user may grasp each of the pull tabs 150 and substantially simultaneously pull the pull tabs 150 to remove the liner 112 from the adhesive patch 110. As a force F is applied to the pull tabs 150 by the user, the first fold 170, the second fold 172, the third fold 174 and the fourth fold 176 cooperate to peel the liner 112 from the adhesive patch 110 starting from the center of the adhesive patch 110 toward the sides 112c, 112d of the adhesive patch 110. As the pull tabs 150 extend beyond the distalmost end 130a of the housing 130, contact to the insertion needle 126 and the adhesive patch 110 by the user is inhibited. When the liner 112 is removed, the user may manipulate the sensor inserter 104 to deploy the physiological characteristic sensor assembly 102 onto the user. The sensor inserter 104 is uncoupled from the physiological characteristic sensor assembly 102.

By providing the removal portion 156 between the first portion 152 and the second portion 154 of the liner 112, the liner 112 is easily removable from the adhesive patch 110 and inadvertent contact to the needle and the adhesive patch 110 is reduced or eliminated. Moreover, by propagating the peel of the liner 112 from the center of the liner 112 outward to the sides 112c, 112d, the adhesive patch 110 remains ready for deployment onto the user.

Figure 7:
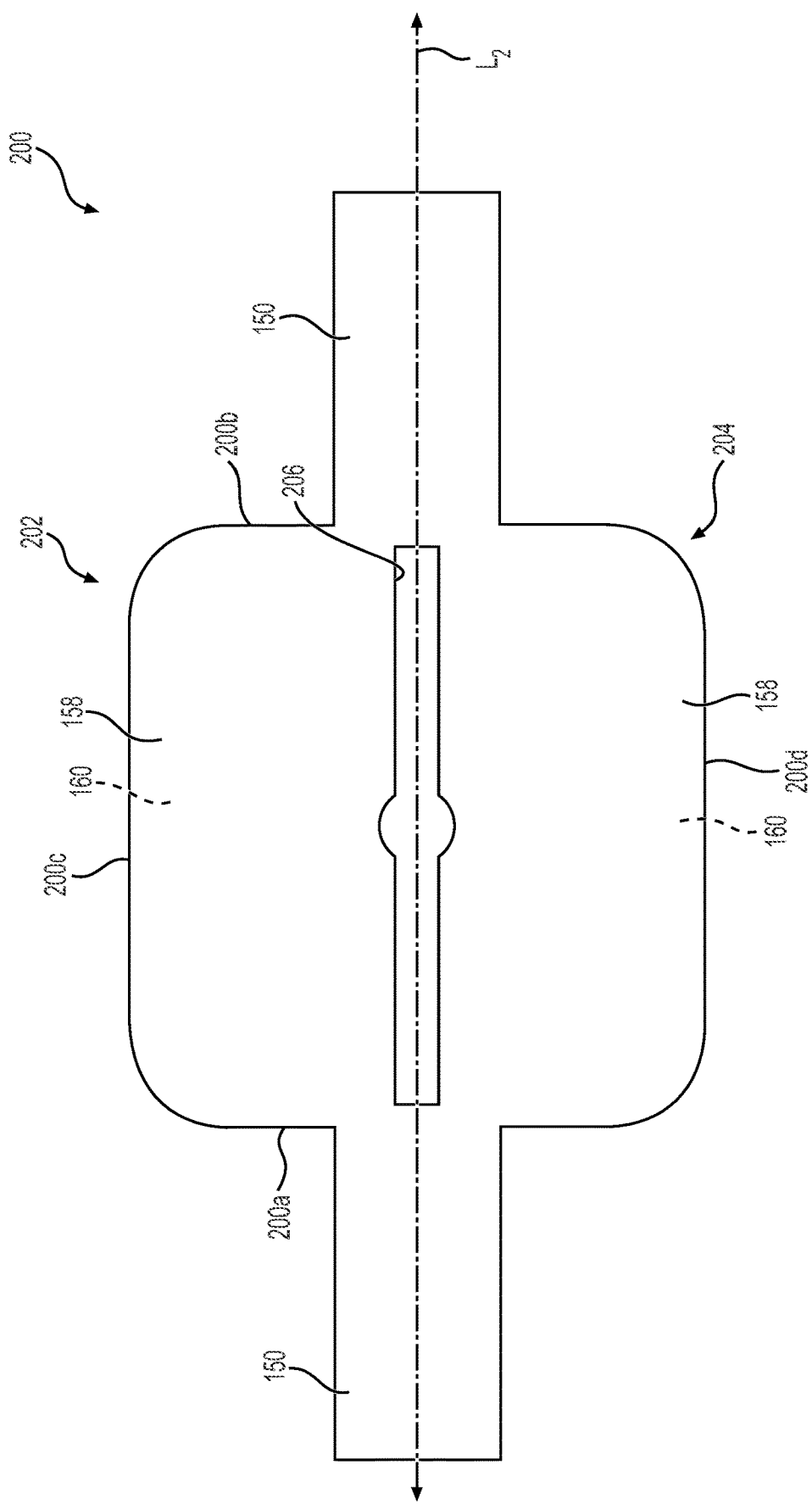
FIG. 7 is a top view of another exemplary liner for use with the sensor introduction system of FIG. 1.

It should be noted that in other embodiments, the liner 112 may be configured differently to enable easy removal of the liner 112 from the adhesive patch 110. For example, with reference to FIG. 7, a liner 200 is shown. As the liner 200 includes the same or similar components as the liner 112 discussed with regard to FIGS. 1-6, the same reference numerals will be used to denote the same or similar components. FIG. 7 is a top view of the liner 200. The liner 200 may be used with the adhesive patch 110 instead of the liner 112 discussed with regard to FIGS. 1-6. In this example, the liner 200 is composed of a silicone coated paper or polymer film and is coupled to the adhesive patch 110 (FIG. 2) so as to cover the adhesive patch 110 (FIG. 2). The liner 200 includes a first portion 202, a second portion 204, a slit 206 and the pull tabs 150. Each of the first portion 202 and the second portion 204 define the first surface 158 opposite the second surface 160. As discussed, the first surface 158 is coupled to and contacts the adhesive patch 110, and the second surface 160 faces the distalmost end 130a of the housing 130 (FIG. 4).

In this example, the slit 206 is defined to extend along a longitudinal axis L2 of the liner 200. The slit 206 is defined between and coupled to each of the first portion 202 and the second portion 204. In one example, the slit 206 is defined between the pull tabs 150. The slit 206 enables the liner 200 to be removed without contacting the insertion needle 126 (FIG. 2). In this example, the liner 200 includes the two pull tabs 150, which extend from opposed ends of the liner 200. Stated another way, the pull tabs 150 extend beyond a first end 200a and an opposite second end 200b of the liner 200. The liner 200 also has a first side 200c opposite a second side 200d. Each of the sides 200c, 200d extend along a respective axis that is parallel to the longitudinal axis L2 of the liner 200, while each of the ends 200a, 200b extend along a respective axis that is perpendicular to the longitudinal axis L2. The pull tabs 150 are sized to extend beyond the distalmost end 130a of the housing 130 (FIG. 2) when the liner 200 is coupled to the adhesive patch 110. By extending beyond the distalmost end 130a, each of the pull tabs 150 may be grasped by the user to remove the liner 200 from the adhesive patch 110 easily and without inadvertently contacting the adhesive patch 110 or the insertion needle 126 of the sensor inserter 104. The pull tabs 150 are defined on the liner 200 so as to be centered on the liner 200 between the first end 200a and the second end 200b. Stated another way, the pull tabs 150 are defined at a center of the liner 200 and are spaced apart from the sides 200c, 200d.

In one example, with the physiological characteristic sensor 108 assembled and coupled to the adhesive patch 110 (FIG. 2) and the liner 200 formed, the first surface 158 of the first portion 202 and the second portion 204 of the liner 200 is coupled to the adhesive patch 110 such that the insertion needle 126 passes through the slit 206. With the physiological characteristic sensor assembly 102 assembled, the physiological characteristic sensor assembly 102 is coupled to the sensor inserter 104 such that the pull tabs 150 fold inward within the housing 130 (FIG. 2). With the physiological characteristic sensor assembly 102 coupled to the sensor inserter 104, the cover 136 is coupled to the housing 130 to enclose the physiological characteristic sensor assembly 102 and the pull tabs 150 of the liner 200. The sensor inserter 104, including the physiological characteristic sensor assembly 102, may be sterilized and shipped to an end user.

Once received, the user may remove the cover 136 to expose the pull tabs 150. The user may grasp each of the pull tabs 150 and substantially simultaneously pull the pull tabs 150 to remove the liner 112 from the adhesive patch 110. As a force is applied to the pull tabs 150 by the user, the liner 200 is peeled from the adhesive patch 110 starting from the center of the liner 200 toward the sides 200c, 200d of the liner 200. As the pull tabs 150 extend beyond the distalmost end 130a of the housing 130, contact to the insertion needle 126 and the adhesive patch 110 by the user is inhibited. When the liner 200 is removed, the user may manipulate the sensor inserter 104 to deploy the physiological characteristic sensor assembly 102 onto the user. The sensor inserter 104 is uncoupled from the physiological characteristic sensor assembly 102.

By providing the slit 206 between the first portion 202 and the second portion 204 of the liner 200, the liner 200 is easily removable from the adhesive patch 110 and inadvertent contact to the needle and the adhesive patch 110 is reduced or eliminated. Moreover, by propagating the peel of the liner 200 from the center of the liner 200 outward to the sides 200c, 200d, the adhesive patch 110 remains ready for deployment onto the user.

Figure 8:
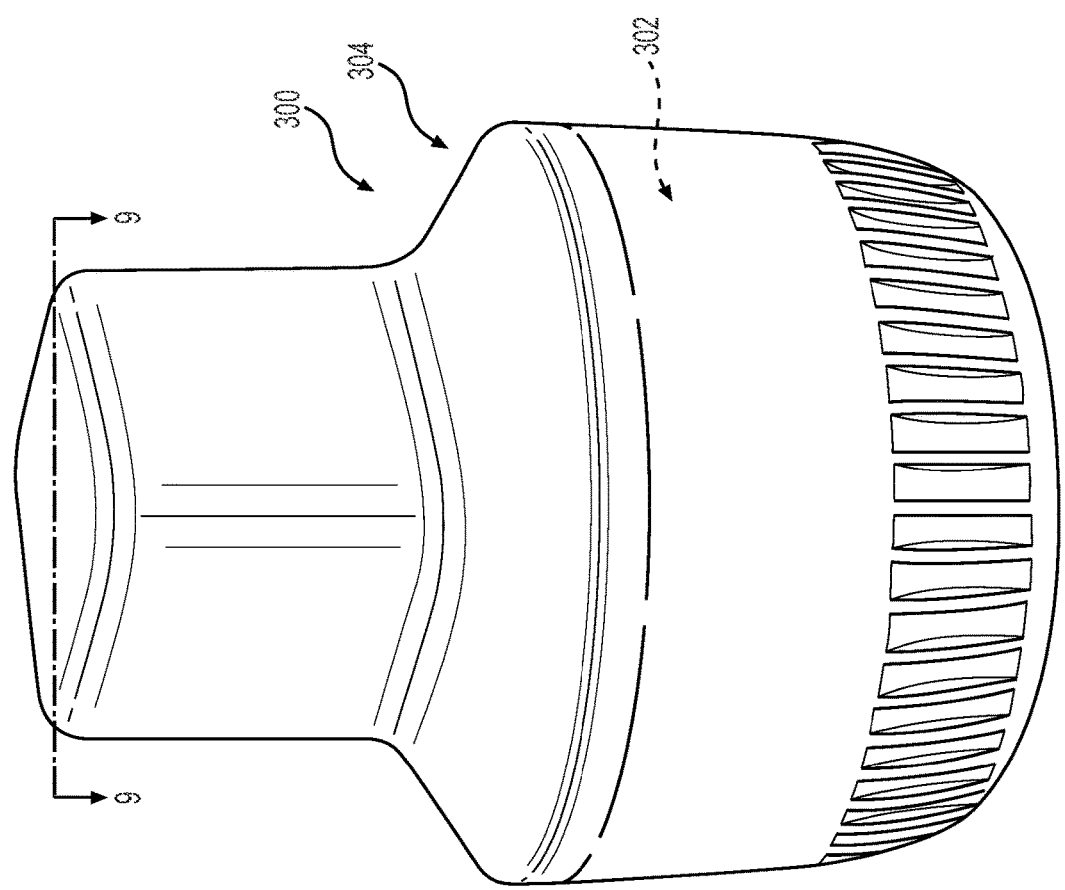
FIG. 8 is a perspective view of another exemplary sensor introduction system that includes a sensor inserter and a physiological characteristic sensor assembly having an adhesive skin patch and an exemplary liner according to various teachings of the present disclosure.

It should be noted that in other embodiments, a liner may be configured differently to enable easy removal from the adhesive patch 110. For example, with reference to FIG. 8, a sensor introduction assembly 300 is shown. As the sensor introduction assembly 300 includes the same or similar components as the sensor introduction assembly 100 discussed with regard to FIGS. 1-6, the same reference numerals will be used to denote the same or similar components. In one example, with reference to FIG. 9, the sensor introduction assembly 300 includes a physiological characteristic sensor assembly 302 and a sensor inserter 304. In this example, the physiological characteristic sensor assembly 302 includes a physiological characteristic sensor 308, the adhesive skin patch or adhesive patch 110 and a liner 312. Generally, the components of the physiological characteristic sensor assembly 302 are coupled together as a single unit. The physiological characteristic sensor assembly 302 and the sensor inserter 304 may be packaged together for use by a consumer. In this example, the sensor inserter 304 and the physiological characteristic sensor 308 comprise the sensor inserter 104 and the physiological characteristic sensor 102 described in commonly assigned U.S. application Ser. No. 16/892,854 to Antonio, et al., the relevant portion of which is incorporated herein by reference. In addition, certain features, aspects, and characteristics of the adhesive patch 110 may be conventional and, as such, will not be described in detail here.

Briefly, the physiological characteristic sensor 308 can be pre-connected as part of a sensor set, which could also include a sensor electronics module (not shown), such as a wireless transmitter that communicates with an infusion pump, a monitor device, or the like, which connects to the physiological characteristic sensor 308 after the insertion or deployment of a portion of the physiological characteristic sensor 308 in the body of the user. In one example, the physiological characteristic sensor 308 includes the glucose sensor 122 and a sensor base 324. It should be noted that the physiological characteristic sensor 308 is not limited to a glucose sensor, but rather, various other physiological characteristic sensors may be employed. The glucose sensor 122 may be provided as an integral part of the sensor base 324. The sensor base 324 gives structural support to the glucose sensor 122, and facilitates entry of the glucose sensor 122 into the body of the user. The glucose sensor 122 is an electrochemical sensor that includes the glucose oxidase enzyme, as is well understood by those familiar with glucose sensor technology. Again, although certain embodiments pertain to glucose sensors, the technology described here can be adapted for use with any one of the wide variety of sensors known in the art. Generally, the glucose sensor 122 is positionable in subcutaneous tissue of the user by an insertion needle 326 of the sensor inserter 304 to measure the glucose oxidase enzyme.

The sensor base 324 is coupled to the sensor inserter 304 and is coupled to the adhesive patch 110. The sensor base 324 is removably coupled to the sensor inserter 304. The sensor base 324 may also feature electrical and physical interfaces and elements that accommodate the sensor electronics module, such as the wireless transmitter that communicates with the infusion pump, the monitor device, or the like. In certain embodiments the sensor base 324 is composed at least in part from a plastic material. For the embodiment described here, the bulk of the sensor base 324 is formed as a molded plastic component. In one example, the sensor base 324 is formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like.

The adhesive patch 110 is coupled to the sensor base 324 and affixes the sensor base 324, and thus, the glucose sensor 122, to an anatomy, such as the skin of the user. The adhesive patch 110 is contained within the sensor inserter 304 during packaging and shipping, and is covered and protected by the liner 312.

The sensor inserter 304 is coupled to the physiological characteristic sensor 308 and is manipulatable by a user to couple the glucose sensor 122 to the user. With continued reference to FIG. 9, the sensor inserter 304 includes a housing 330, a sensor carrier 332, one or more biasing members or springs and a lid or cap 336. In one example, the housing 330 surrounds the physiological characteristic sensor assembly 302 and encloses the physiological characteristic sensor assembly 302 to enable sterilization of the physiological characteristic sensor assembly 302, for example. The housing 330 may include one or more features, such as movable tabs, that cooperate with the sensor carrier 332 to deploy the physiological characteristic sensor 308 into the anatomy. The sensor carrier 332 is coupled to the physiological characteristic sensor 308, and is movable relative to the housing 330 to deploy the physiological characteristic sensor 308 into the anatomy. For example, the application of a force to the housing 330 may bias the tabs to release the sensor carrier 332 to enable a spring associated with the sensor carrier 332 to drive the sensor carrier 332 to deploy the physiological characteristic sensor 308 into the anatomy. Once released, another spring cooperates with the sensor carrier 332 to move a needle retractor relative to the housing 330. The cap 336 surrounds a circumferentially open end of the housing 330, and encloses the housing 330.

In this example, the cap 336 includes a projection or post 338. The post 338 extends inwardly from the cap 336 and defines a channel 340. The channel 340 receives the insertion needle 326 of the sensor inserter 104 and the glucose sensor 122. In this example, a magnet 342 is coupled about an opening 340a of the channel 340. The magnet 342 cooperates with a magnetic field sensor of the physiological characteristic sensor 308 to activate the physiological characteristic sensor 308 once the cap 336, including the magnet 342, is removed. The magnet 342 may be coupled about the opening 340a via a press-fit, welding, etc., such that the magnet 342 is fixed to the cap 336.

Figure 9:
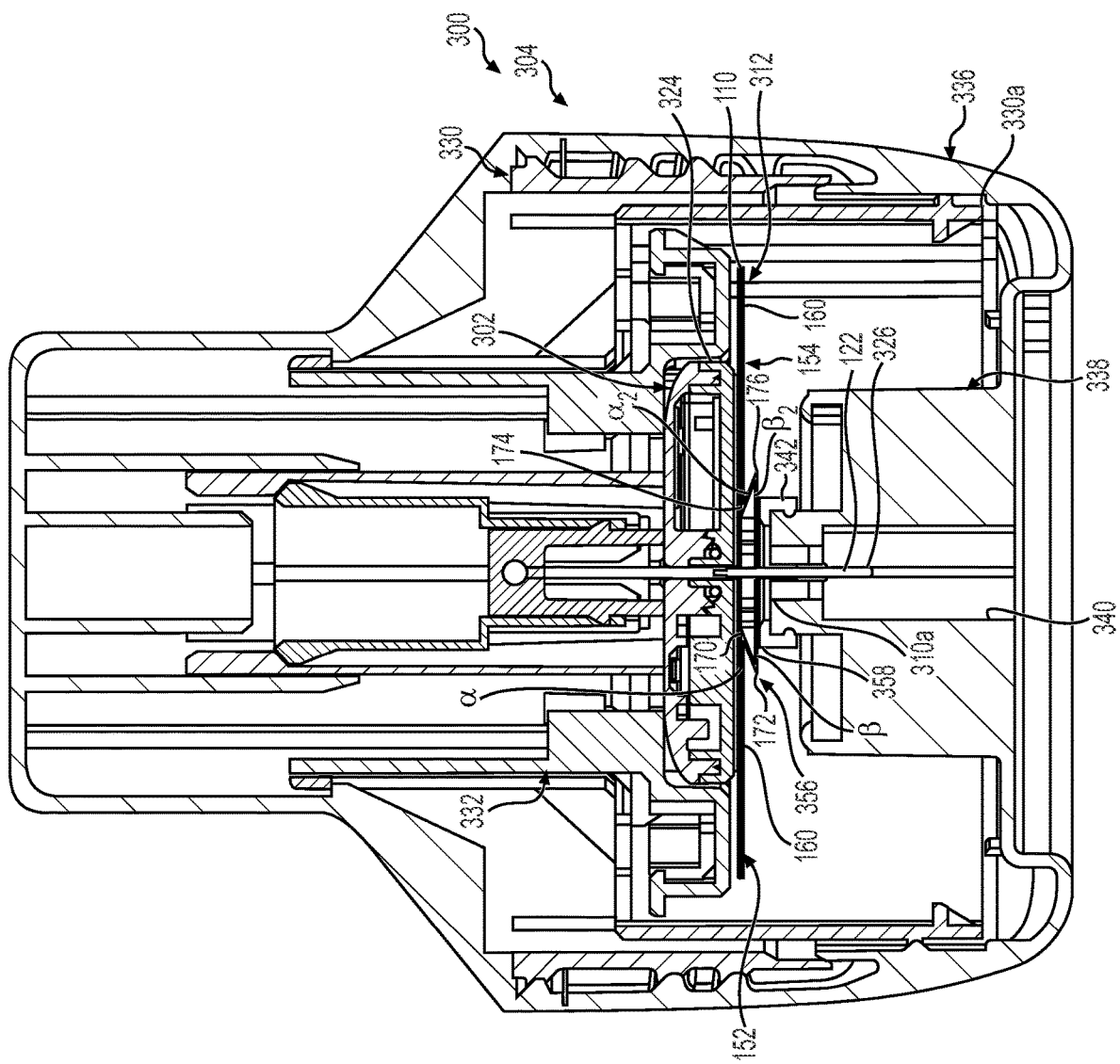
FIG. 9 is a cross-sectional view of the sensor introduction system of FIG. 8, taken along line 9-9 of FIG. 8.
Figure 10:
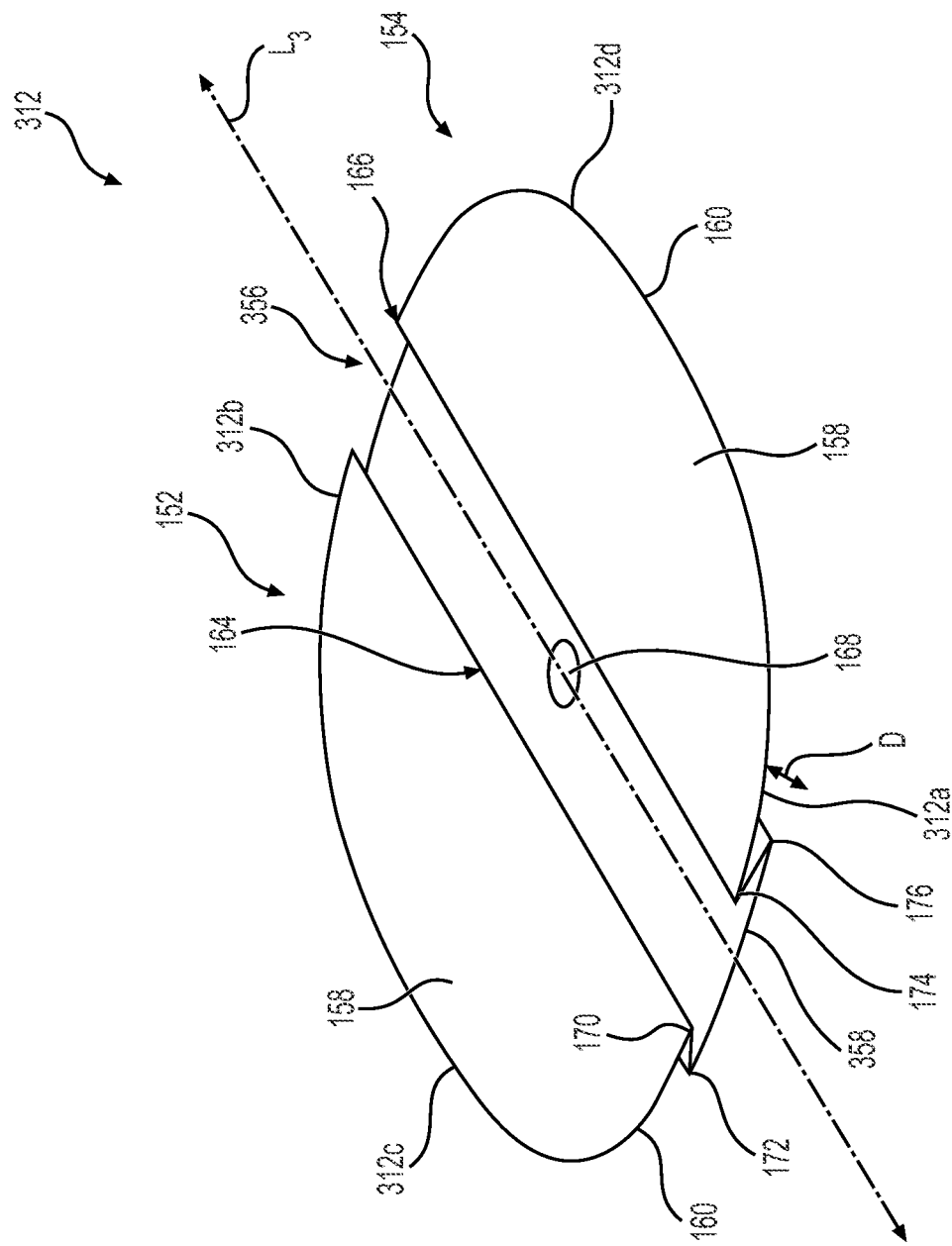
FIG. 10 is a perspective view of the liner associated with the sensor introduction system of FIG. 8.
Figure 11A:
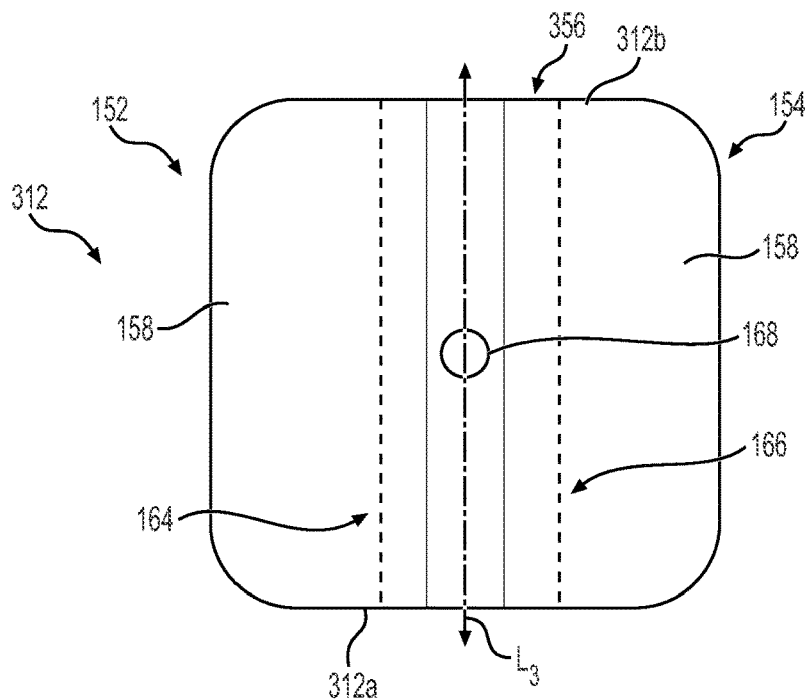
FIG. 11A is a top view of the liner of FIG. 10.

In one example, with reference to FIG. 10, the liner 312 is shown in greater detail. FIG. 10 is a perspective view of the liner 312. In this example, the liner 312 is composed of a silicone coated paper or polymer film and is coupled to the adhesive patch 110 so as to cover the adhesive patch (FIG. 9). The liner 312 includes the first portion 152, the second portion 154 and a removal portion 356. The first portion 152 is defined along a first side 312c of the liner 312, and the second portion 154 is defined along a second side 312d of the liner 312, the first side 312c opposite the second side 312d. Each of the sides 312c, 312d extend along a respective axis that is parallel to a longitudinal axis L3 of the liner 312, while each of ends 312a, 312b extend along a respective axis that is perpendicular to the longitudinal axis L3. Each of the first portion 152 and the second portion 154 define the first surface 158 opposite the second surface 160. With reference to FIG. 11A, the first surface 158 is coupled to the adhesive patch 110 (FIG. 9), and the second surface 160 (FIG. 11B) faces the distalmost end 330a of the housing 330 (FIG. 9).

Figure 11B:
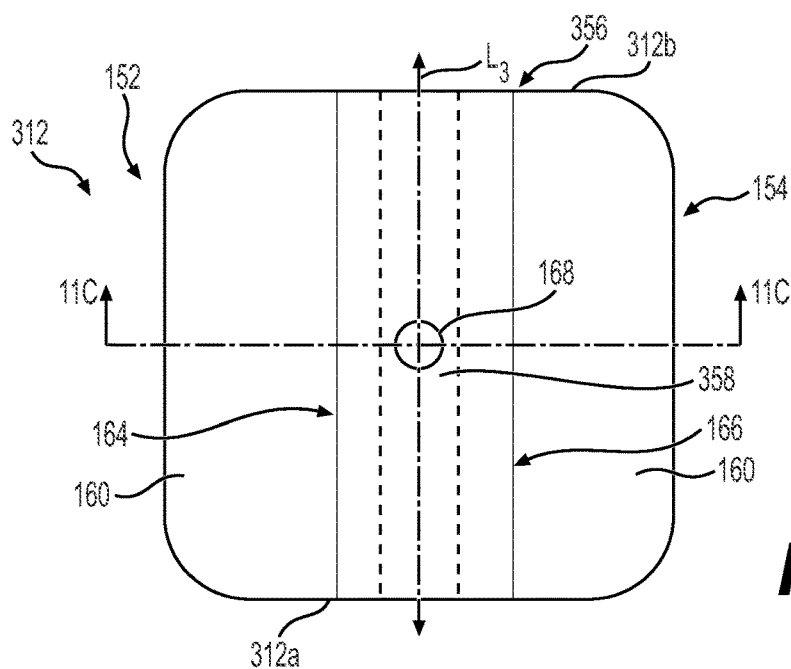
FIG. 11B is a bottom view of the liner of FIG. 10.
Figure 11C:
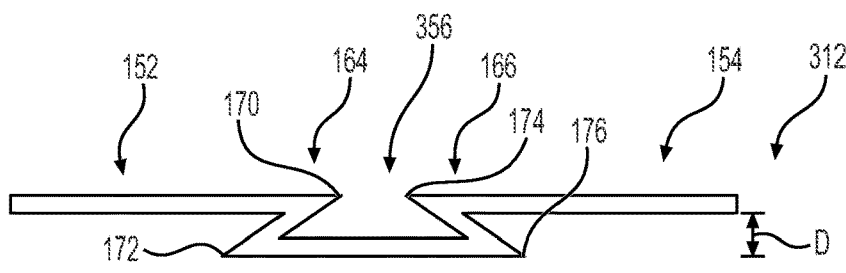
FIG. 11C is a cross-sectional view of the liner of FIG. 10, taken along line 11C-11C of FIG. 11B.

In this example, with reference to FIGS. 11A and 11B, the removal portion 356 is defined to extend along a longitudinal axis L3 of the liner 312. Generally, the liner 312 is symmetric about the longitudinal axis L3. The removal portion 356 is defined between and coupled to each of the first portion 152 and the second portion 154. In one example, the removal portion 356 is defined between the first portion 152 and the second portion 154 and extends from a first end 312a to a second end 312b of the liner 312. The removal portion 356 includes the first coupling portion 164, the second coupling portion 166, a coupling surface 358 (FIG. 11B) and defines the central bore 168. The central bore 168 is sized to enable the liner 312 to be positioned about the insertion needle 126. The first coupling portion 164 is defined to couple the removal portion 356 to the first portion 152. With reference to FIG. 11C, the first coupling portion 164 is defined by the first fold 170 and the second fold 172 defined in the liner 312. The second coupling portion 166 is defined to couple the removal portion 356 to the second portion 154. The second coupling portion 166 is defined by the third fold 174 and the fourth fold 176 defined in the liner 312. The first fold 170, the second fold 172, the third fold 174 and the fourth fold 176 cooperate to distance the removal portion 356 from the adhesive patch 110 such that the removal portion 356 is not coupled to and is spaced apart from the adhesive patch 110. In one example, with reference to FIG. 11C, the removal portion 356 is spaced the distance D away from the first surface 158. The first fold 170 is also spaced apart from the second fold 172 by the distance D, and the third fold 174 is spaced apart from the fourth fold 176 by the distance D.

By providing the removal portion 356 uncoupled from the adhesive patch 110, a removal force associated with separating the liner 312 from the adhesive patch 110 is reduced. In addition, the use of the first coupling portion 164 and the second coupling portion 166 ensures that the liner 312 is removed from the adhesive patch 110 starting from at the first fold 170 and the third fold 174 toward the sides 312c, 312d of the liner 312, which ensures that the liner 312 is removed from the adhesive patch 110 without inadvertently folding or rolling the adhesive patch 110. Stated another way, the peel of the liner 312 from the adhesive patch 110 starts along the longitudinal axis L3 at a center of the liner 312 between the first portion 152 and the second portion 154 or along the removal portion 356, and propagates outward to the sides 312c, 312d of the liner 312. By starting at the center of the liner 312 and propagating outward, the removal of the liner 312 reduces a likelihood of the adhesive patch 110 folding upon itself. In other words, if the liner 312 were removed from the sides 312c, 312d inward, the removal of the liner 312 may cause the adhesive patch 110 to fold, which may be undesirable for adhering to the body of the user. Thus, the removal portion 156 of the liner 312, by peeling from the center of the adhesive patch 110 toward the sides 312c, 312d, ensures that the adhesive patch 110 remains suitable for coupling to the user.

With reference to FIG. 9, the coupling surface 358 couples the liner 312 to the cap 336. In one example, the coupling surface 358 of the liner 312 is coupled to the magnet 342 of the cap 336. In this example, the coupling surface 358 about the perimeter of the central bore 168 is coupled to the magnet 342 about a circumference of the magnet 342. The coupling surface 358 is coupled to the magnet 342 via any suitable technique, including adhesives, for example, double sided adhesive tape, ultrasonic welding, etc. Generally, the coupling surface 358 is coupled to the magnet 342 such that a removal of the cap 336 from the housing 330 causes a removal of the liner 312 from the adhesive patch 110. Thus, in this example, the liner 312 is removable simultaneously with the removal of the cap 336, eliminating the need for the user to remove the liner 312. Thus, the liner 312 reduces a workload of a user in coupling the physiological characteristic sensor 308 to the user's anatomy.

In one example, with the physiological characteristic sensor 308 assembled and coupled to the adhesive patch 110 and the liner 312 formed with the first fold 170, the second fold 172, the third fold 174 and the fourth fold 176, the first surface 158 of the first portion 152 and the second portion 154 of the liner 312 is coupled to the adhesive patch 110 such that the insertion needle 126 passes through the central bore 168. With the physiological characteristic sensor assembly 302 assembled, and the springs and the monitor support 132 coupled to the housing 330, the physiological characteristic sensor assembly 302 is coupled to the sensor inserter 304. With the physiological characteristic sensor assembly 302 coupled to the sensor inserter 304, the cap 336 is coupled to the housing 330 such that the magnet 342 is coupled to the coupling surface 358 of the liner 312, via contact between a double sided adhesive coupled to the magnet 342 and the coupling surface 358, for example. The sensor inserter 304, including the physiological characteristic sensor assembly 302, may be sterilized and shipped to an end user.

Once received, the user may remove the cap 336. As the user removes the cap 336, since the liner 312 is coupled to the cap 336, the user also removes the liner 312. As the cap 336 is removed, the first fold 170, the second fold 172, the third fold 174 and the fourth fold 176 cooperate to peel the liner 312 from the adhesive patch 110 starting from the center of the liner 312 toward the sides 312c, 312d of the liner 312. As the liner 312 is removed with the removal of the cap 336, contact to the insertion needle 126 and the adhesive patch 110 by the user is inhibited. When the liner 312 is removed, the user may manipulate the sensor inserter 304 to deploy the physiological characteristic sensor assembly 302 onto the user. The sensor inserter 304 is uncoupled from the physiological characteristic sensor assembly 302.

By providing the removal portion 356 between the first portion 152 and the second portion 154 of the liner 312, and the liner 312 coupled to the cap 336, the liner 312 is easily removable from the adhesive patch 110 and inadvertent contact to the needle and the adhesive patch 110 is reduced or eliminated. Moreover, by propagating the peel of the liner 312 from the center of the liner 312 outward to the sides 312c, 312d, the adhesive patch 110 remains ready for deployment onto the user.

It should be noted that in other embodiments, the liner 312 may be configured differently to enable easy removal of the liner 312 from the adhesive patch 110. For example, with reference to FIG. 12, another exemplary liner 412 for use with the sensor introduction assembly 300 is shown. As the liner 412 includes the same or similar components as the liner 312 discussed with regard to FIGS. 8-11C and the liner 112 discussed with regard to FIGS. 1-6, the same reference numerals will be used to denote the same or similar components. FIG. 12 is a schematic cross-sectional view, taken from the perspective of line 9-9 of FIG. 8. In this example, the liner 412 is composed of a silicone coated paper or polymer film and is coupled to the adhesive patch 110 so as to cover the adhesive patch (FIG. 13). The liner 412 includes the first portion 152, the second portion 154 and a removal portion 456. The first portion 152 is defined along a first side 412c of the liner 412, and the second portion 154 is defined along a second side 412d of the liner 412, the first side 412c opposite the second side 412d. Each of the sides 412c, 412d extend along a respective axis that is parallel to a longitudinal axis L4 of the liner 412, while each of ends 412a, 412b extend along a respective axis that is perpendicular to the longitudinal axis L4. Each of the first portion 152 and the second portion 154 define the first surface 158 opposite the second surface 160. The first surface 158 is coupled to the adhesive patch 110, and the second surface 160 faces the cap 336.

In this example, with reference to FIG. 13, the removal portion 456 is defined to extend along the longitudinal axis L4 of the liner 412. Generally, the liner 412 is symmetric about the longitudinal axis L4. The removal portion 456 is defined between and coupled to each of the first portion 152 and the second portion 154. In one example, the removal portion 356 is defined between the first portion 152 and the second portion 154 and extends from the first end 412a to the second end 412b of the liner 412. The removal portion 456 includes the first coupling portion 164, the second coupling portion 166, a coupling surface 458, a tether 460 and defines the central bore 168. The central bore 168 is sized to enable the liner 412 to be positioned about the insertion needle 126. The first coupling portion 164 is defined to couple the removal portion 456 to the first portion 152. With reference to FIG. 12, the first coupling portion 164 is defined by the first fold 170 and the second fold 172 defined in the liner 412. The second coupling portion 166 is defined to couple the removal portion 456 to the second portion 154. The second coupling portion 166 is defined by the third fold 174 and the fourth fold 176 defined in the liner 412. The first fold 170, the second fold 172, the third fold 174 and the fourth fold 176 cooperate to distance the removal portion 456 from the adhesive patch 110 such that the removal portion 456 is not coupled to and is spaced apart from the adhesive patch 110. In one example, the removal portion 456 is spaced the distance D away from the first surface 158.

By providing the removal portion 456 uncoupled from the adhesive patch 110, a removal force associated with separating the liner 412 from the adhesive patch 110 is reduced. In addition, the use of the first coupling portion 164 and the second coupling portion 166 ensures that the liner 412 is removed from the adhesive patch 110 starting from at the first fold 170 and the third fold 174 toward the sides 412c. 412d of the liner 412, which ensures that the liner 412 is removed from the adhesive patch 110 without inadvertently folding or rolling the adhesive patch 110. Stated another way, the peel of the liner 412 from the adhesive patch 110 starts along the longitudinal axis L4 at a center of the liner 412 between the first portion 152 and the second portion 154 or along the removal portion 456, and propagates outward to the sides 412c, 412d of the liner 412. By starting at the center of the liner 412 and propagating outward, the removal of the liner 412 reduces a likelihood of the adhesive patch 110 folding upon itself. In other words, if the liner 412 were removed from the sides 412c, 412d inward, the removal of the liner 412 may cause the adhesive patch 110 to fold, which may be undesirable for adhering to the body of the user. Thus, the removal portion 456 of the liner 412, by peeling from the center of the liner 412 toward the sides 412c, 412d, ensures that the adhesive patch 110 remains suitable for coupling to the user.

The coupling surface 458 couples the liner 412 to the tether 460. In one example, the coupling surface 458 of the liner 412 is coupled to the tether 460 via any suitable technique, including adhesives, for example, double sided adhesive tape, ultrasonic welding, etc. Generally, the coupling surface 458 is coupled to the tether 460 such that a removal of the cap 336 from the housing 330 causes a removal of the liner 412 from the adhesive patch 110. As will be discussed, in this example, the liner 412 is removable simultaneously with the removal of the cap 336 due to the tether 460, eliminating the need for the user to remove the liner 412. Thus, the liner 412 reduces a workload of a user in coupling the physiological characteristic sensor 308 to the user's anatomy.

The tether 460 couples the liner 412 to the cap 336. In one example, the tether 460 is composed of a polymer film. In this example, the tether 460 is formed separate or discrete from the liner 412, however, in other embodiments, the tether 460 may be integrally formed with or one-piece with the liner 412. The tether 460 includes a first tether end 462 opposite a second tether end 464. The first tether end 462 is coupled to the coupling surface 458 of the liner 412, while the second tether end 464 is coupled to the cap 336. With reference to FIG. 14, the tether 460 is shown in greater detail. The first tether end 462 is opposite the second tether end 464 and is spaced apart from the second tether end 464 by a tether body 465. The first tether end 462 includes a tether coupling surface 466 and a first tether bore 468. The tether coupling surface 466 couples the tether 460 to the liner 412. In one example, the tether coupling surface 466 is fixedly coupled to the coupling surface 458 of the liner 412 via adhesives, such as double sided adhesive tape, ultrasonic welding, etc. such that the liner 412 moves with a movement of the tether 460. The first tether bore 468 is defined to enable the tether 460 to be positioned about the insertion needle 326 of the sensor inserter 304 (FIG. 12). Generally, the first tether end 462 is coupled to the liner 412 such that the first tether bore 468 is coaxially aligned with the central bore 168 of the liner 412.

The tether body 465 interconnects the first tether end 462 and the second tether end 464. The tether body 465 has a length LT, which is sized to enable the removal of the cap 336 to remove the liner 412 via the tether 460. In one example, the length LT is about 2.0 centimeters (cm) to about 5.0 centimeters (cm). When the cap 336 is coupled to the housing 330 (FIG. 12), the tether body 465 may fold upon itself to be received in a space defined between the housing 330 and the cap 336. With brief reference to FIG. 12, the second tether end 464 is coupled about the post 338 of the cap 336, and in this example, the second tether end 464 is coupled about an end 338a of the post 338 that is opposite the opening 340a. Generally, the second tether end 464 is coupled about the post 338 such that a lip 338b of the post 338 retains the second tether end 464 on the post 338. Thus, the end 338a of the post 338 may define a tether receiving channel 339, which retains the second tether end 464 on the cap 336, while enabling the cap 336 to rotate relative to the tether 460. By retaining the second tether end 464 with the lip 338b, which inhibits a removal of the second tether end 464 from the post 338, the cap 336 is rotatable relative to the tether 460 to uncouple the cap 336 from the housing 330.

With reference back to FIG. 14, the second tether end 464 defines a second tether bore 470 and a slit 472. The second tether bore 470 is sized to receive the post 338 and to be received within the tether receiving channel 339 (FIG. 12). Generally, the second tether bore 470 has a diameter D1, which is different and less than a diameter D2 (FIG. 12) of the lip 338b such that the lip 338b retains the second tether end 464 on the post 338. As the diameter D2 of the lip 338b is greater than the diameter D1 of the second tether bore 470, the slit 472 enables the second tether end 464 to be positioned over the post 338. In this regard, with reference to FIG. 15, the slit 472 is in communication with the second tether bore 470 so that as the second tether bore 470 is positioned onto the post 338, the slit 472 opens to enlarge the diameter of the second tether bore 470 to enable the second tether end 464 to be coupled to the post 338.

In one example, with the physiological characteristic sensor 308 assembled and coupled to the adhesive patch 110 and the liner 412 formed with the first fold 170, the second fold 172, the third fold 174 and the fourth fold 176, the first tether end 462 is coupled to the coupling surface 458 of the liner 412 such that the first tether bore 468 is coaxially aligned with the central bore 168. The first surface 158 of the first portion 152 and the second portion 154 of the liner 412 is coupled to the adhesive patch 110 such that the insertion needle 126 passes through the central bore 168 and the first tether bore 468. With the physiological characteristic sensor assembly 302 assembled, and the springs and the monitor support 132 coupled to the housing 330, the physiological characteristic sensor assembly 302 is coupled to the sensor inserter 304. With the physiological characteristic sensor assembly 302 coupled to the sensor inserter 304, the second tether bore 470 is positioned over the post 338 of the cap 336. The slit 472 enables the second tether bore 470 to pass over the lip 338b (FIG. 12) so that the second tether end 464 is received within the tether receiving channel 339 (FIG.

12). With the second tether end 464 coupled to the cap 336, the cap 336 is coupled to the housing 330 to enclose the physiological characteristic sensor assembly 302 and the liner 412. The coupling of the cap 336 to the housing 330 causes the tether body 465 to fold upon itself to be contained between the housing 330 and the cap 336. The sensor inserter 304, including the physiological characteristic sensor assembly 302, may be sterilized and shipped to an end user.

Once received, with reference to FIG. 12, the user may remove the cap 336. In the example of the cap 336 being coupled to the housing 330 with a threaded connection, the user may rotate the cap 336 relative to the housing 330. As the second tether end 464 is retained within the tether receiving channel 339, the cover rotates relative to the tether 460. Once the cap 336 is uncoupled from the housing 330, as the user removes the cap 336 further from the housing, the tether 460 removes the liner 412 from the adhesive patch 110. In this regard, as the distance between the cap 336 and the housing 330 increases, the tether body 465 unfolds and the first tether end 462 begins to peel the liner 412. The continued application of force to the liner 412 from the tether 460 causes the first fold 170, the second fold 172, the third fold 174 and the fourth fold 176 to cooperate to peel the liner 412 from the adhesive patch 110 starting from the center of the liner 412 toward the sides 412c, 412d of the liner 412. As the liner 412 is removed with the removal of the cap 336, contact to the insertion needle 126 and the adhesive patch 110 by the user is inhibited. When the liner 412 is removed, the user may manipulate the sensor inserter 304 to deploy the physiological characteristic sensor assembly 302 onto the user. The sensor inserter 304 is then uncoupled from the physiological characteristic sensor assembly 302.

By providing the removal portion 456 between the first portion 152 and the second portion 154 of the liner 412, and the liner 412 coupled to the cap 336 via the tether 460, the liner 412 is easily removable from the adhesive patch 110 and inadvertent contact to the needle and the adhesive patch 110 is reduced or eliminated. Moreover, by propagating the peel of the liner 412 from the center of the liner 412 outward to the sides 412c, 412d, the adhesive patch 110 remains ready for deployment onto the user.

Figure 16:
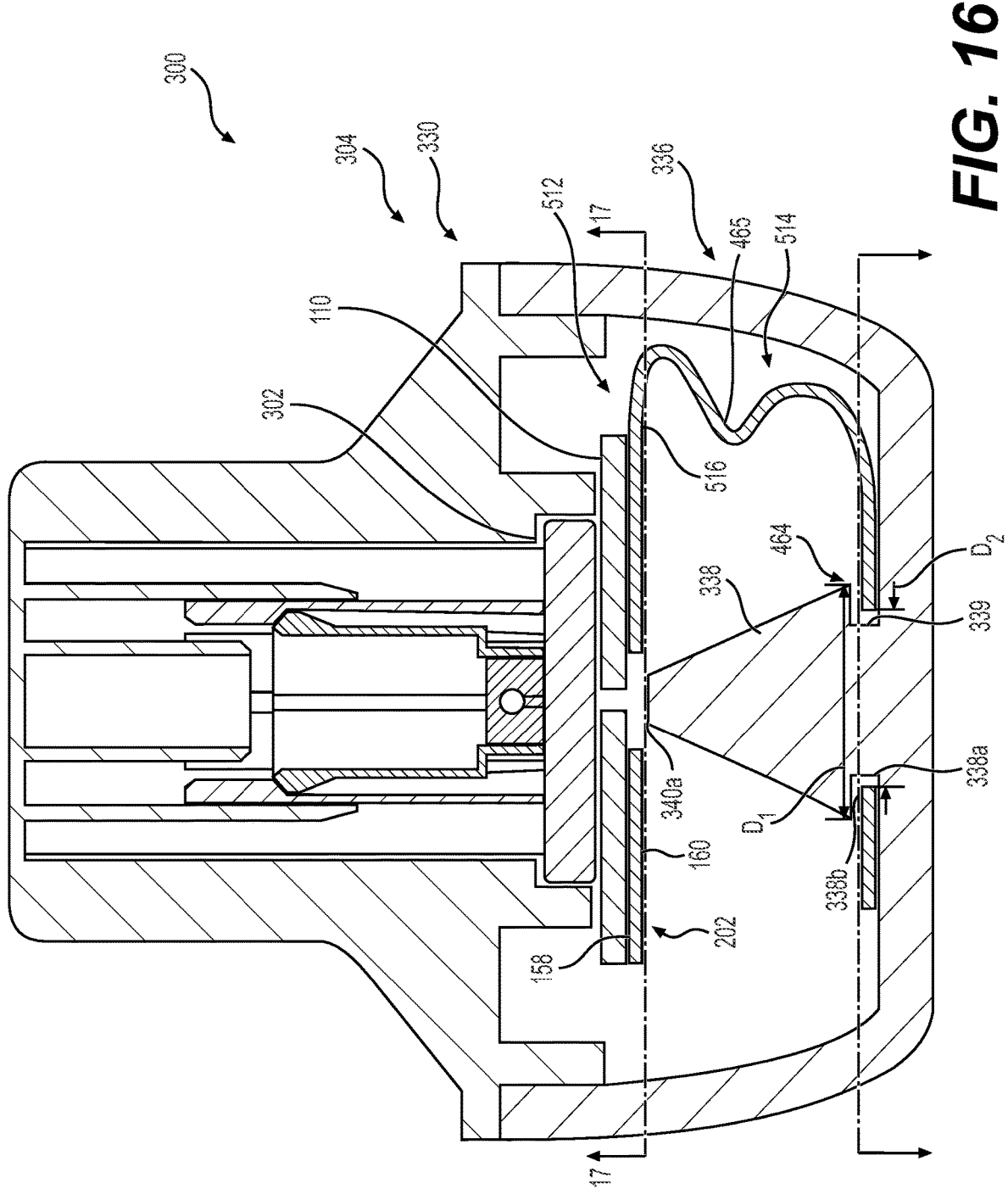
FIG. 16 is a perspective view of another exemplary sensor introduction system that includes a sensor inserter and a physiological characteristic sensor assembly having an adhesive skin patch and an exemplary liner according to various teachings of the present disclosure.
Figure 17:
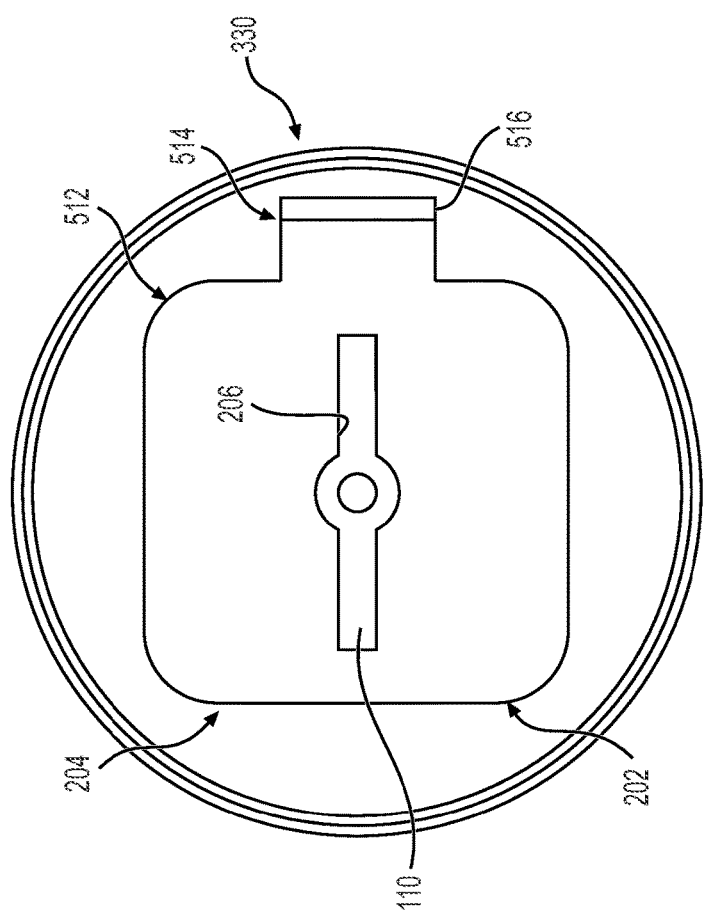
FIG. 17 is a cross-sectional view of the sensor introduction system of FIG. 16, taken along line 17-17 of FIG. 16, which illustrates the liner coupled to the adhesive skin patch and a first tether end of a tether associated with the liner coupled to the liner.

It should be noted that in other embodiments, a liner may be configured differently to enable easy removal of the liner from the adhesive patch 110. For example, with reference to FIG. 16, another exemplary liner 512 for use with the sensor introduction assembly 300 is shown. As the liner 512 includes the same or similar components as the liner 412 discussed with regard to FIGS. 12-15 and the liner 200 discussed with regard to FIG. 7, the same reference numerals will be used to denote the same or similar components. FIG. 16 is a schematic cross-sectional view, taken from the perspective of line 9-9 of FIG. 8. In this example, the liner 512 is composed of a silicone coated paper or polymer film, and is coupled to the adhesive patch 110 so as to cover the adhesive patch (FIG. 17). In this example, with reference to FIG. 18, the liner 512 includes the first portion 202, the second portion 204, the slit 206 and a tether 514. The first portion 202 is defined along a first side 512c of the liner 512, and the second portion 204 is defined along a second side 512d of the liner 512, the first side 512c opposite the second side 512d. Each of the sides 512c, 512d extend along a respective axis that is parallel to a longitudinal axis L5 of the liner 512, while each of ends 512a, 512b extend along a respective axis that is perpendicular to the longitudinal axis L5. Each of the first portion 202 and the second portion 204 define the first surface 158 opposite the second surface 160. As discussed, the first surface 158 is coupled to and contacts the adhesive patch 110, and the second surface 160 faces the cap 336 (FIG. 16). Thus, in this example, the first portion 202 and the second portion 204 cooperate to cover the adhesive patch 110.

In this example, the slit 206 is defined to extend along the longitudinal axis L5 of the liner 512. Generally, the liner 512 is symmetric about the longitudinal axis L5. The slit 206 is defined between and coupled to each of the first portion 202 and the second portion 204. In one example, the slit 206 is defined to extend between the first end 512a of the liner 512 to the opposite second end 512b. The slit 206 enables the liner 512 to be removed without contacting the insertion needle 126 (FIG. 2).

In this example, the tether 514 is integrally formed with the liner 512. The tether 514 is coupled to the cap 336 such that a removal of the cap 336 from the housing 330 causes a removal of the liner 512 from the adhesive patch 110. Thus, in this example, the liner 512 is removable simultaneously with the removal of the cap 336 due to the tether 514, eliminating the need for the user to remove the liner 512. Thus, the liner 512 reduces a workload of a user in coupling the physiological characteristic sensor 308 to the user's anatomy.

The tether 514 includes a first tether end 516 opposite the second tether end 464. The first tether end 516 is coupled to the first portion 202 and the second portion 204 at the second end 512b of the liner 512, while the second tether end 464 is coupled to the cap 336. The first tether end 516 is opposite the second tether end 464 and is spaced apart from the second tether end 464 by the tether body 465. In certain embodiments, the slit 206 may extend into the first tether end 516. The tether body 465 interconnects the first tether end 516 and the second tether end 464. When the cap 336 is coupled to the housing 330 (FIG. 16), the tether body 465 may fold upon itself to be received in a space defined between the housing 330 and the cap 336.

With brief reference to FIG. 16, the second tether end 464 is coupled about the post 338 of the cap 336, and in this example, the second tether end 464 is coupled about the end 338a of the post 338 that is opposite the opening 340a. As discussed, the end 338a of the post 338 may define a tether receiving channel 339, which retains the second tether end 464 on the cap 336, while enabling the cap 336 to rotate relative to the tether 514. By retaining the second tether end 464 with the lip 338b, which inhibits a removal of the second tether end 464 from the post 338, the cap 336 is rotatable relative to the tether 514 to uncouple the cap 336 from the housing 330.

With reference back to FIG. 18, the second tether end 464 defines the second tether bore 470 and the slit 472. The second tether bore 470 is sized to receive the post 338 and to be received within the tether receiving channel 339 (FIG. 16). With refence to FIG. 19, the slit 472 is in communication with the second tether bore 470 so that as the second tether bore 470 is positioned onto the post 338, the slit 472 opens to enlarge the diameter of the second tether bore 470 to enable the second tether end 464 to be coupled to the post 338.

Figure 18:
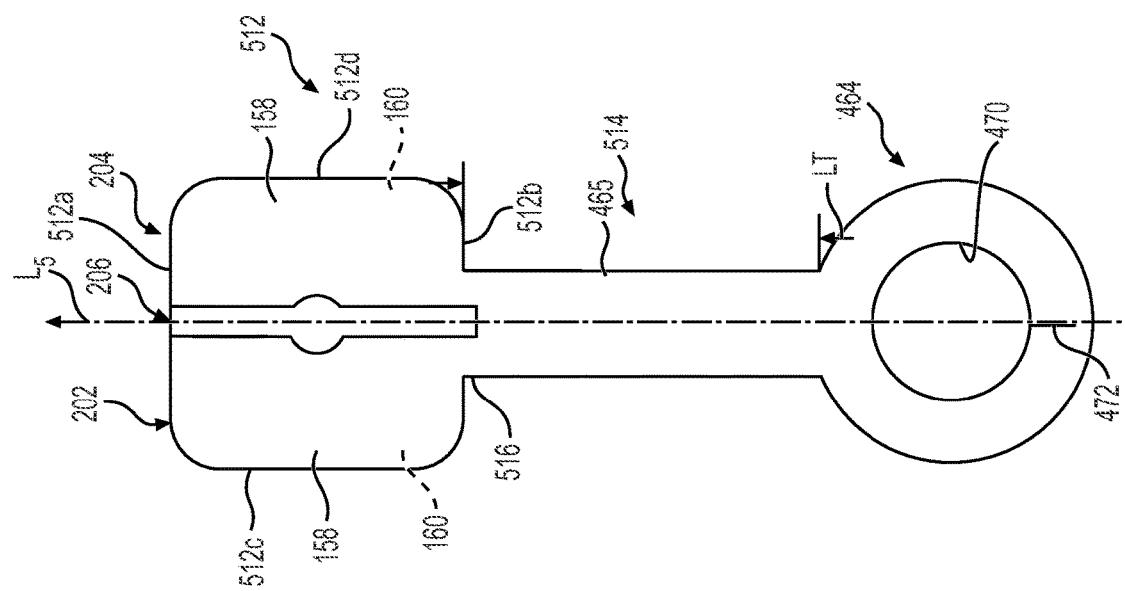
FIG. 18 is a front view of the tether associated with the liner of FIG. 16.
Figure 19:
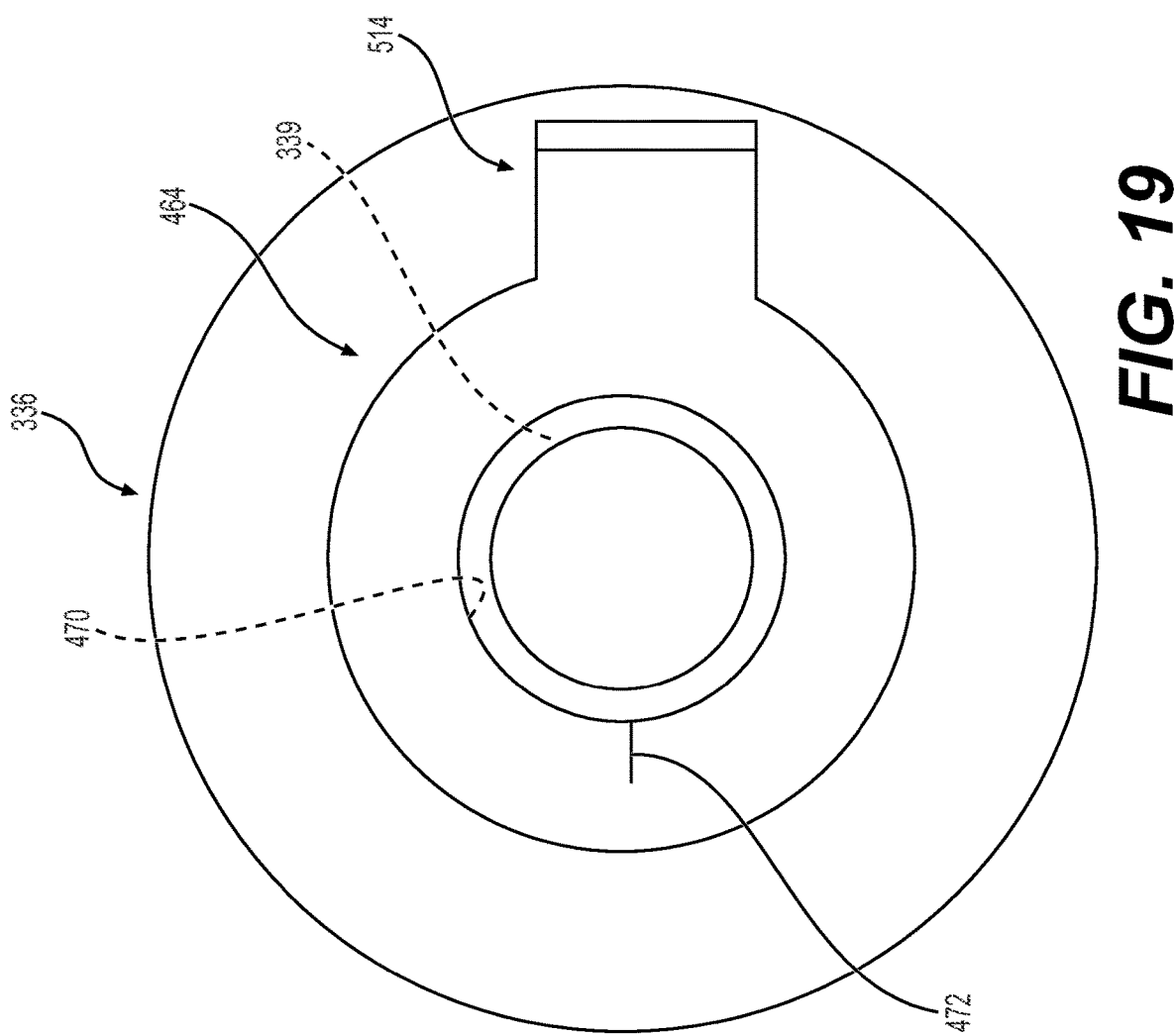
FIG. 19 is a cross-sectional view of the sensor introduction system of FIG. 16, taken along line 19-19 of FIG. 16, which illustrates a second tether end of the tether associated with the liner coupled to a cover of the sensor inserter.

In one example, with reference to FIG. 17, with the physiological characteristic sensor 308 assembled and coupled to the adhesive patch 110 and the liner 512 formed with the tether 514, the first surface 158 of the first portion 202 and the second portion 204 (FIG. 18) of the liner 412 is coupled to the adhesive patch 110 such that the insertion needle 126 passes through the central bore 168 and the slit 206 (FIG. 18). With the physiological characteristic sensor assembly 302 assembled, and the springs and the monitor support 132 coupled to the housing 330, the physiological characteristic sensor assembly 302 is coupled to the sensor inserter 304. With the physiological characteristic sensor assembly 302 coupled to the sensor inserter 304, the second tether bore 470 is positioned over the post 338 of the cap 336. The slit 472 enables the second tether bore 470 to pass over the lip 338b (FIG. 19) so that the second tether end 464 is received within the tether receiving channel 339 (FIG. 16). With the second tether end 464 coupled to the cap 336, the cap 336 is coupled to the housing 330 to enclose the physiological characteristic sensor assembly 302 and the liner 512. The coupling of the cap 336 to the housing 330 causes the tether body 465 to fold upon itself to be contained between the housing 330 and the cap 336. The sensor inserter 304, including the physiological characteristic sensor assembly 302, may be sterilized and shipped to an end user.

Once received, with reference to FIG. 16, the user may remove the cap 336. In the example of the cap 336 being coupled to the housing 330 with a threaded connection, the user may rotate the cap 336 relative to the housing 330. As the second tether end 464 is retained within the tether receiving channel 339, the cap 336 rotates relative to the tether 514. Once the cap 336 is uncoupled from the housing 330, as the user removes the cap 336 further from the housing, the tether 514 removes the liner 512 from the adhesive patch 110. In this regard, as the distance between the cap 336 and the housing 330 increases, the tether body 465 unfolds and the first tether end 462 begins to peel the first portion 202 and the second portion 204 from the adhesive patch 110. The continued application of force to the first portion 202 and the second portion 204 from the tether 514 causes the liner 512 to be removed from the adhesive patch 110. As the liner 512 is removed with the removal of the cap 336, contact to the insertion needle 126 and the adhesive patch 110 by the user is inhibited. When the liner 512 is removed, the user may manipulate the sensor inserter 304 to deploy the physiological characteristic sensor assembly 302 onto the user. The sensor inserter 304 is then uncoupled from the physiological characteristic sensor assembly 302. Thus, by providing the liner 512 coupled to the cap 336 via the tether 514, the liner 512 is easily removable from the adhesive patch 110 and inadvertent contact to the needle and the adhesive patch 110 is reduced or eliminated.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An arrangement of a liner and an adhesive skin patch of a physiological characteristic sensor deployed with a sensor inserter having a housing with a removable cover, the liner comprising:
    a first portion spaced apart from a second portion, and each of the first portion and the second portion including a surface coupled to the adhesive skin patch; and
    a removal portion to couple the liner to the removable cover of the sensor inserter such that a separation of the removable cover from the housing removes the liner from the adhesive skin patch, the removal portion defined between the first portion and the second portion, the removal portion having a first coupling portion defined by at least a first fold between the removal portion and the first portion, a second coupling portion defined by a least a fold between the removal portion and the second portion, and the removal portion is spaced apart and uncoupled from the adhesive skin patch,
    wherein the removal portion further comprises a tether configured to be coupled between the removal portion and the removable cover.

2. The liner of claim 1, wherein the first coupling portion includes the first fold and a second fold, and the first fold is spaced apart from the second fold by a distance.

3. The liner of claim 2, wherein the second coupling portion includes the fold and a fourth fold between the removal portion and the second portion, the fold and the fourth fold spaced apart by a second distance.

4. The liner of claim 1, wherein the tether has a first tether end coupled to the removal portion and a second tether end to couple to a post of the removable cover.

5. The liner of claim 4, wherein the second tether end includes a bore in communication with a slit, and the bore and the slit cooperate to couple the second tether end to the removable cover such that the removable cover is rotatable relative to the tether.

6. A sensor introduction assembly, comprising:
    a physiological characteristic sensor having an adhesive skin patch;
    a sensor inserter having a housing for deploying the physiological characteristic sensor, the sensor inserter having a housing with a removable cover; and
    a liner coupled to the adhesive skin patch and to the removable cover, the liner including a tether that extends between the liner and the removable cover such that a separation of the removable cover from the housing removes the liner from the adhesive skin patch,
    wherein the removable cover includes a post that defines a tether receiving channel, and an end of the tether is received within the tether receiving channel to couple the tether to the removable cover.

7. The sensor introduction assembly of claim 6, wherein the sensor inserter includes an introducer needle, and the liner defines a slot to position the liner about the introducer needle.

8. The sensor introduction assembly of claim 6, wherein the end of the tether defines a bore in communication with a slit to position the end of the tether within the tether receiving channel such that the removable cover is rotatable relative to the tether.

9. The sensor introduction assembly of claim 6, wherein the liner includes a first portion spaced apart from a second portion by a removal portion, each of the first portion and the second portion include a surface to couple the liner to the adhesive skin patch and the removal portion is spaced apart and uncoupled from the adhesive skin patch.

10. The sensor introduction assembly of claim 9, wherein the removal portion of the liner includes a first coupling portion defined by a first fold and a second fold between the removal portion and the first portion and a second coupling portion defined by a third fold and a fourth fold between the removal portion and the second portion.

11. The sensor introduction assembly of claim 9, wherein the tether is coupled between the removal portion and the removable cover.

12. The sensor introduction assembly of claim 11, wherein the tether has a first tether end coupled to the removal portion and the end coupled to the removable cover.

13. An arrangement of a and with an adhesive skin patch of a physiological characteristic sensor deployed with a sensor inserter having a housing with a removable cover, the liner comprising:
a surface coupled to the adhesive skin patch; and
a removal portion to couple the liner to the removable cover of the sensor inserter such that a separation of the removable cover from the housing removes the liner from the adhesive skin patch, the removal portion including a tether that is coupled between the removal portion and the removable cover, the tether has a first tether end coupled to the removal portion and a second tether end to be coupled to a post of the removable cover, the second tether end includes a bore in communication with a slit, and the bore and the slit cooperate to couple the second tether end to the post of the removable cover such that the removable cover is rotatable relative to the tether.

14. The liner of claim 1, wherein the liner is composed of a silicon coated paper or polymer film.

* * * * *